United States Patent [19]

Nishimiya et al.

[11] Patent Number: 5,204,143

[45] Date of Patent: Apr. 20, 1993

[54] PROCESS FOR TREATING METAL SURFACE

[75] Inventors: Nobuyuki Nishimiya; Toshiyuki Sekiya, both of Shizuoka, Japan

[73] Assignee: Fuji Photo Film Co., Ltd., Kanagawa, Japan

[21] Appl. No.: 503,751

[22] Filed: Apr. 3, 1990

[30] Foreign Application Priority Data

Apr. 3, 1989 [JP] Japan ................................... 1-84193

[51] Int. Cl.$^5$ .............................................. B05D 3/02
[52] U.S. Cl. .................................. 427/387; 427/388.1; 428/457; 430/275
[58] Field of Search ..................... 427/387, 327, 388.1; 430/275; 428/457

[56] References Cited

U.S. PATENT DOCUMENTS 4,656,097  4/1987  Claffey et al. ................... 427/327 X
4,753,827  6/1988  Yoldas et al. ......................... 427/387
4,808,483  2/1989  Nakasaji et al. ................. 427/327 X

FOREIGN PATENT DOCUMENTS

WO88/05473  7/1988  PCT Int'l Appl. .

Primary Examiner—Michael Lusigan
Attorney, Agent, or Firm—Burns, Doane, Swecker & Mathis

[57] ABSTRACT

The present invention relates to a process for treating a metal surface wherein a liquid composition comprising an inorganic polymer is applied to the metal surface. The inorganic polymer is produced by hydrolyzing and then polycondensing, in an organic solvent, an organometallic compound having an organic functional group and a group capable of being hydrolyzed and then polycondensed in an organic solvent.

According to the present invention, the metal surface per se is made chemically reactive by fixing functional groups on the metal surface an is very useful, for example, as a support for making a presensitized lithographic plate.

14 Claims, No Drawings

PROCESS FOR TREATING METAL SURFACE

BACKGROUND OF THE INVENTION

The present invention relates to a process for treating a metal surface. In particular, the present invention relates to a process for treating a metal surface to impart a chemical reactivity thereto.

Techniques of making the metal surface functional have been widely known.

For example, techniques of forming a protective film for physically or chemically protecting the metal surface or a functional film for imparting optical properties (such as coloring, light absorbance, reflectivity, antireflectivity and photoconductivity) have been proposed. These surface treatment techniques can be conducted by various methods wherein a particular chemical substance is applied to the metal surface.

On the contrary, methods of imparting chemical functions such as chemical reactivity to the metal surface are limited. For example, a method of making the surface oxidation-reactive by forming a perovskite layer on the surface of an electrode is well known. The chemical reactivity is due to the surface compound. This reaction proceeds catalytically, but the surface per se is neither reacted nor changed. Namely, there are a few methods capable of imparting the chemical reactivity due to the functional group to the surface so as to cause the surface per se to be involved in the chemical reaction. In other words, there are a few methods of obtaining the surface having an intended distribution of functional groups and each of them has its own defect.

For example, a method wherein the surface is treated with plasma to introduce a functional group into the surface has defects that the treatment should be conducted in vacuo, that the control of the process parameter is troublesome and that an excellent reproducibility cannot be easily obtained by the surface treatment. Further, this method is usually employed for the treatment of a polymer film, but not for the treatment of the metal surface.

The surface treatment with a silane coupling agent has defects that the adhesion is poor because the wettability with the hydrophilic surface is poor, that the control of the reactions such as condensation dehydration on the surface to be treated is not easy and the surface is apt to be stained with the catalyst or the like, and that microscopically, an organic substance is excessive in a part of the inorganic support surface to which the silane coupling agent was applied and, therefore, it is unsuitable for use in applications where a well-balanced lipophilic and hydrophilic property is necessary.

Although it was reported that a hydrophilic functional group is formed on the surface of a silicon rubber by introduction of a heavy ion an expensive apparatus is required and the material to be treated is limited and therefore this method is not popular.

SUMMARY OF THE INVENTION

Therefore, the object of the present invention is to provide a process for the surface treatment which satisfies all the following necessary conditions:

(1) a functional group is formed on the metal surface to impart chemical reactivity thereto, (2) the kind and density of the functional group can be controlled, (3) a wet process is employed or, in other words, vacuum, plasma or gas phase ion is not employed, (4) the surface treatment can be conducted with good reproducibility, and (5) wettability or lipophile/hydrophile balance of the treated surface can be controlled.

After intensive investigations made for the purpose of attaining the above-described object, the inventors have found that the object can be attained by coating a metal surface with a liquid composition and, if necessary, drying it, the liquid composition comprising an inorganic polymer produced by hydrolyzing and simultaneously polycondensing an organometallic compound having an intended organic functional group and a group capable of being hydrolyzed and polycondensed in a solution, if necessary, in the presence of a catalyst, while the intended organic functional group is kept unreacted, and the metal of the organometallic compound forming the metal-oxygen-metal structure of the resulting inorganic polymer. The present invention has been completed on the basis of this finding. The desired functions can be obtained because the inorganic polymer having the metal-oxygen-metal bond obtained by the hydrolysis and subsequent polycondensation is closely adhered to a support to be treated and the intended functional group remains on the surface of the treated support.

DETAILED EXPLANATION OF THE INVENTION

The organometallic compounds usable in the liquid composition in the present process are represented by the following general formula (1):

$$A_m M(OR)_n \qquad (1)$$

wherein:
- A represents an organic functional group,
- M represents a metal,
- R represents a hydrogen atom and an alkyl group, or a functional group which can be replaced with an alkyl group in an organic solvent, and
- m and n each represents a positive integer satisfying the following formula: $1 \leq m+n \leq 6$ and when m is two or more, A's may be the same as or different from each other.

The organometallic compounds of the general formula (1) can be used either singly or in combination of two or more of them. Further, they can be used in the form of a mixture with an organometallic compound of the following formula (2) having no organic functional group A:

$$M(OR)_n \qquad (2)$$

wherein M and R are as defined in the above formula (1) and n represents a positive integer satisfying the following formula: $1 \leq n \leq 6$.

The organometallic compounds wherein a part or all of the OR groups of the general formulae (1) and (2) are replaced by a halogen atom, can be suitably used in the present invention. Specifically speaking, precursor organometallic compounds which can produce the organometallic compounds represented by the general formulae (1) and (2) by the action of water or an alcohol. The halogen atom includes F, Cl, Br and I.

In addition, the organometallic compounds wherein a part of or all of the OR groups in the general formulae (1) and (2) are hydrolyzed and polycondensed to form a Metal-Oxygen-Metal bond in a molecule, can be used in the present invention.

When a mixture of the organometallic compounds of the general formulae (1) and (2) is hydrolyzed and polycondensed to form a polymer or colloidal polymer having the metal-oxygen-metal bond and then the metal surface is treated with the liquid composition thus obtained, an OH group from the compound (2) and in some cases, both an OH group derived from the compound (1) and an OH group derived from the compound (2) are fixed on the metal surface as well as the functional group A derived from the compound (1). The OH group is formed by the hydrolysis of the OR group in the general formulae (1) and (2).

The density of the organic functional group A on the metal surface treated with the liquid composition can be controlled by adjusting the concentration of the liquid composition or the relative amounts of the compounds represented by the formulae (1) and (2).

The metal M in the general formulae (1) and (2) may be any of Li, Na, K, Rb, Cs, Be, Mg, Ca, Sr, Ba, Sc, Y, rare earth metals, Ti, V, Cr, Mn, Fe, Co, Ni, Cu, Zn, Zr, Nb, Mo, Hf, Ta, W, Ru, Rh, Pd, Ir, Pt, B, Al, Ga, In, Tl, Si, Ge, Sn, Pb, P, As, Sb and Bi. Among them, Al, Si and Ti are preferred, because the starting materials of them are easily available on the market.

The organic functional group A includes a hydrogen atom, an alkyl group, an arkyl group, an aryl group, an alkenyl group, a propargyl group, an alkoxy group, an epoxyalkyl group, a silyl group, a siloxy group and a hydroxy group. The group A may be substituted by, for example, a halogen atom, an alkyl group, an aryl group, a hydroxy group, an alkoxy group, an aryloxy group, an acyloxy group, a carbamoyloxy group, an alkoxycarbonyl group, an acyl group, a carbamoyl group, an alkoxycarbonyloxy, a carboxyl group, a propargyl group, an amino group, an alkylamino group, an acylamino group, a ureido group, a carbamate group, a diazonio group, a diazo group, an azo group, a mercapto group, an alkylthio group, a sulfonyl group, a sulfo group, a cyano group, an isocyanate group, a thiocyanate group, a sulfamoyl group, a nitro group, a silyl group and a siloxy group.

The specific examples of the group A are as follows:

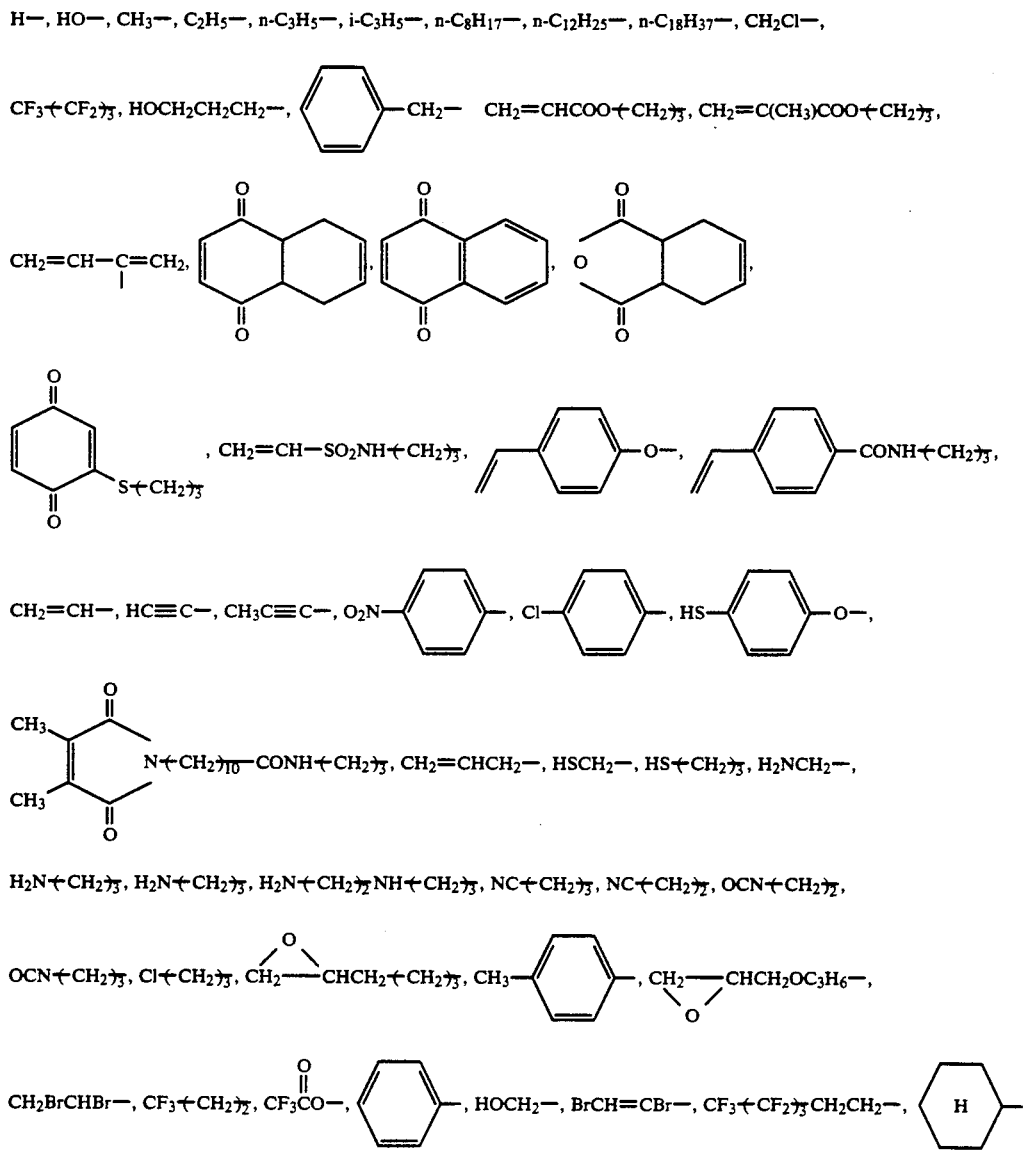

-continued
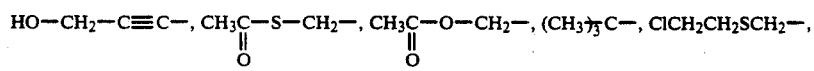
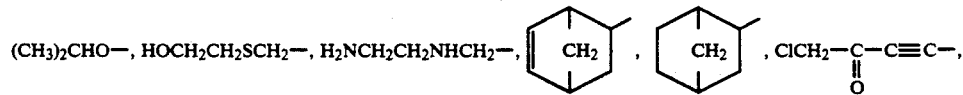
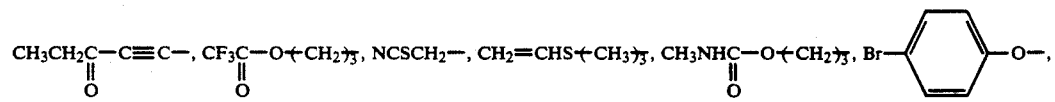
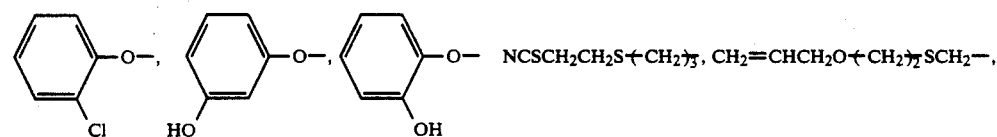
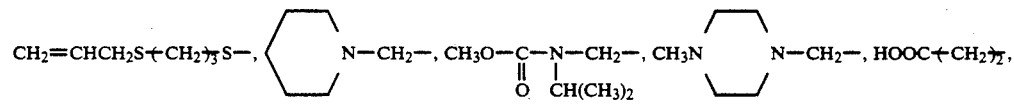
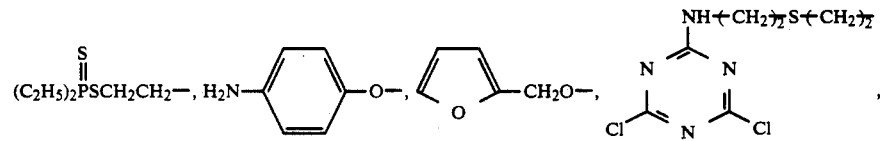
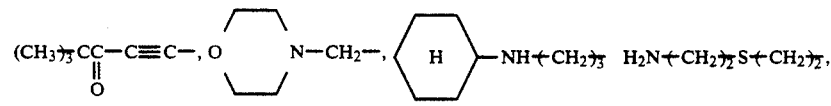
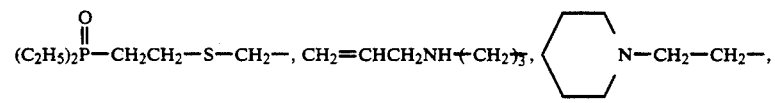
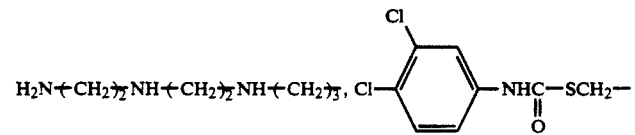
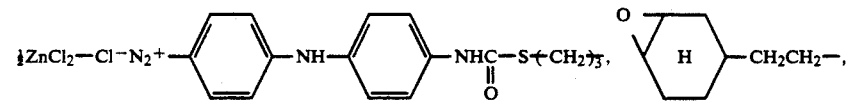
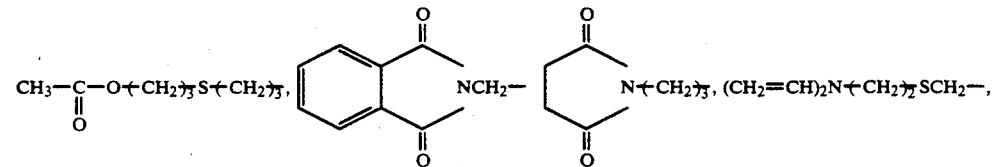

-continued

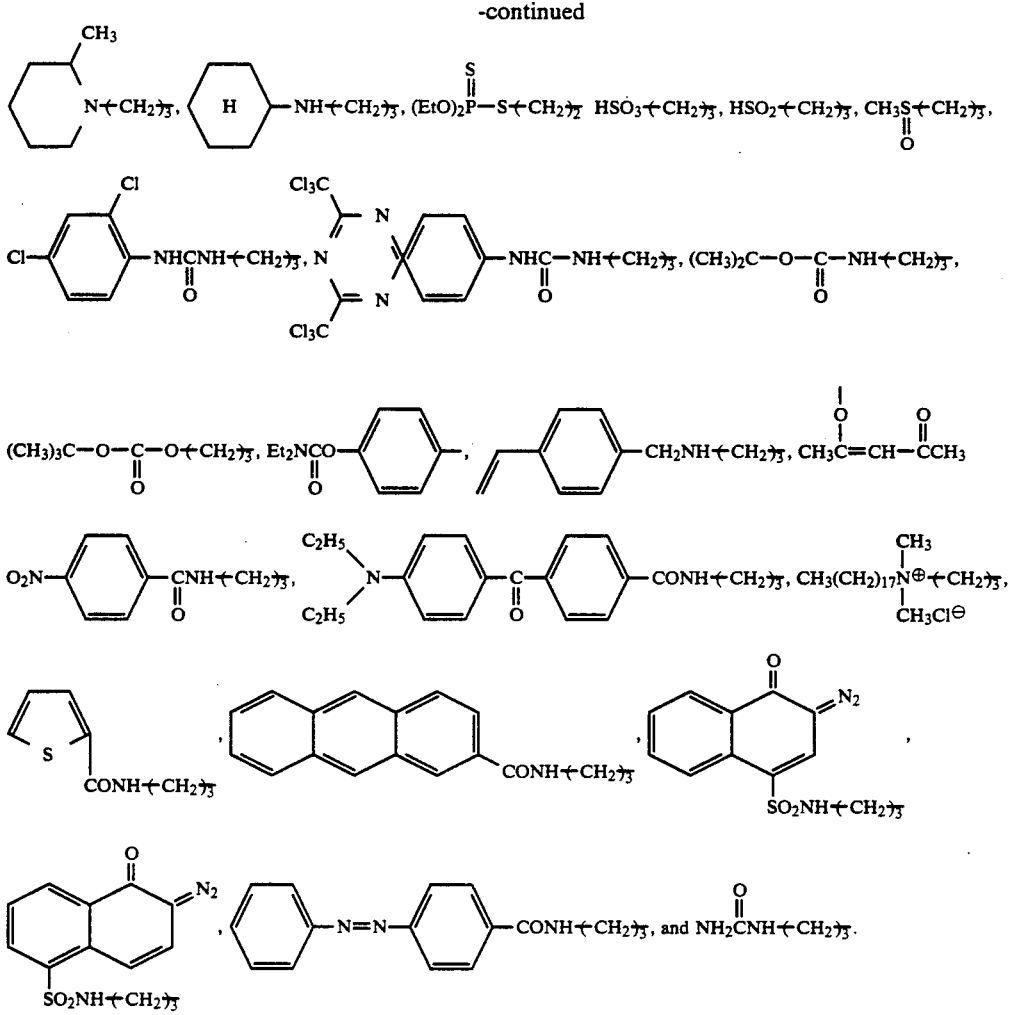

The R group of the general formulae (1) and (2) represents a hydrogen atom and an alkyl group, or a functional group which can be replaced by an alkyl group in an organic solvent. When two or more OR groups are used, the R groups may be the same as or different from each other.

The alkyl group may be any of linear, branched or cyclic forms. The examples thereof include $CH_3-$, $C_2H_5-$, $n-C_3H_7-$, $i-C_3H_7-$, $n-C_4H_9-$, $sec-C_4H_9-$, $tert-C_4H_9-$ and a cyclohexyl group.

The functional group as R includes, for example, a halogen atom such as Cl or Br and an organic acid residual group. While an acetyl group is convenient for use as an organic acid residual group, acyl groups having more carbon atoms than the acetyl group can be used.

The replacement between the functional group R and an alkyl group includes the case wherein the R group is replaced by an alkyl group or the case wherein the OR group is replaced by —O— alkyl group.

OR is not limited to those of unidentate ligand type but includes also polydentate alkoxide residues such as diol and triol residues and polydentate organic acid residues such as oxalic acid and succinic acid residues.

Examples of the compounds of the general formula (1) include the following ones:

$H_2N(CH_2)_2NH(CH_2)_3-Si(OCH_3)_3$ $CH_2=CH-Si(OCOCH_3)_3$ $CH_2=CH-Si(OC_2H_5)_3$ $H_2N(CH_2)_3-Si(OC_2H_5)_3$ $OCNCH_2CH_2CH_2-Si(OCH_3)_3$

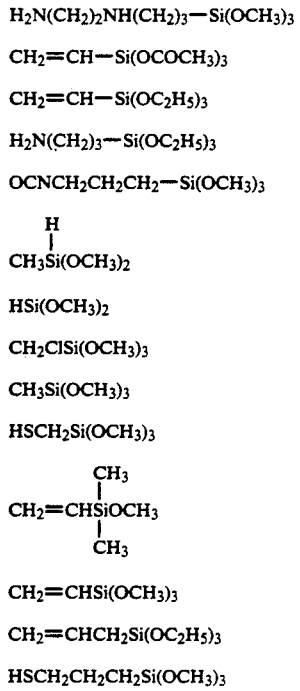

$HSi(OCH_3)_2$ $CH_2ClSi(OCH_3)_3$ $CH_3Si(OCH_3)_3$ $HSCH_2Si(OCH_3)_3$ $$CH_2=CHSiOCH_3 \text{ with } CH_3, CH_3 \text{ substituents}$$

$CH_2=CHSi(OCH_3)_3$ $CH_2=CHCH_2Si(OC_2H_5)_3$ $HSCH_2CH_2CH_2Si(OCH_3)_3$

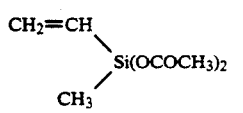

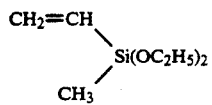

(CH₂=CH)₂Si(OC₂H₅)₂

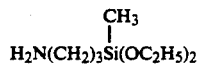

NC(CH₂)₂Si(OC₂H₅)₃

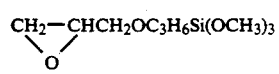

CH₂=CHCH₂NH(CH₂)₃Si(OCH₃)₃

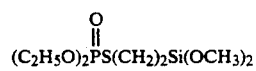

CH₂=C(CH₃)COO(CH₂)₃Si(OCH₃)₃

CH₂=CHCOO(CH₂)₃Si(OCH₃)₃

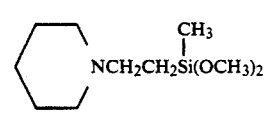

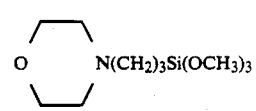

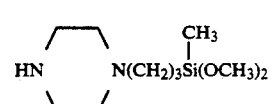

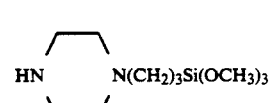

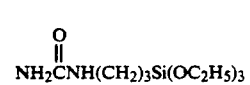

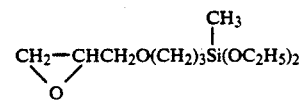

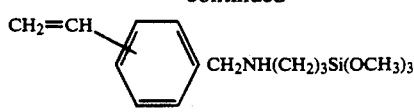

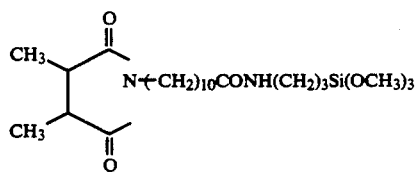

CH≡CSi(OC₂H₅)₃

CH₂=CHSi(OCOCH₃)₃

(C₅H₇O₂)₂Ti(OC₃H₇)₂

(C₅H₇O₂)₂V(OC₃H₇)₂

(C₅H₇O₂)₂Ba(OC₂H₅)₂

Examples of the compounds of the general formula (2) include the following ones:

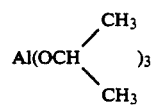

Si(OCH₃)₄

Si(OC₂H₅)₄

Si(OCOCH₃)₄

Si(OC₃H₇)₄

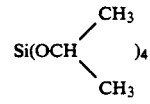

Si(OC₄H₉)₄

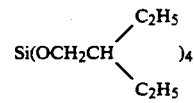

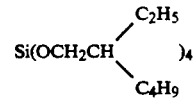

Ti(OC₃H₇)₄

Ti(OC₄H₉)₄

Zr(OC₃H₇)₄

V(OC₂H₅)₅

W(OC₂H₅)₆

The organic solvents particularly usable in the hydrolysis and polycondensation of the organometallic compounds of the general formulae (1) and (2) are, for example, methanol, ethanol, i-propanol, hexane, cyclohexane, benzene, toluene, 1,4-dioxane, tetrahydrofuran, methyl ethyl ketone, ethylene glycol dimethyl ether, ethylene glycol monomethyl ether, ethylene glycol diethyl ether, propylene glycol monomethyl ether, acetylacetone, N,N-dimethylformamide and monoethanolamine. The organic solvents are, of course, not limited to these solvents. These solvents can be used singly or as a mixture thereof.

When the organometallic compounds of the general formulae (1) and (2) are hydrolyzed in an organic solvent, it is possible to use water remaining in the organic solvent as a hydrolyzing agent. However, in order to control the preparation of the liquid composition of the present invention so as to finish the preparation within a prescribed time, water is preferably added to the organic solvent in an amount of 0.5 to 1000 mol per mol of the organometallic compound. When the amount of water is less than this range, the hydrolysis and the subsequent polycondensation reaction proceed quite slowly and several days are usually necessitated prior to the treatment of the metal surface. On the contrary, when the amount of water exceeds this range, the adhesion of the resulting composition to the metal surface is poor, the composition has a poor storability, and it easily gels and therefore it is difficult to stably coat the composition.

Water can act not only as a hydrolyzing agent, but also as a solvent for the liquid composition. Under the conditions that the hydrolyzing rate of the compounds of the general formulae (1) and (2) is so slow that gellation does not occur so easily, the liquid composition of the present invention can be prepared in an aqueous medium.

The reaction temperature usually ranges from room temperature to about 100° C. It is also possible to conduct the reaction at a temperature higher than the boiling point of the solvent by means of a reflux condenser.

The time necessitated for the hydrolysis and polycondensation reaction varies depending on the reaction temperature. The reaction temperature is suitably selected depending on the purpose, since a reaction which necessitates several days at ambient temperature is completed in several hours at 80° C.

The catalysts usable, if necessary, include acids such as hydrochloric acid and acetic acid as well as bases such as ammonia and tetramethylammonium hydroxide. The amount of the catalyst is usually about 0.01 to 0.1 mol per mol of the organometallic compounds of the general formulae (1) and (2). Sometimes it is preferably more than 0.1 mol. The amount of the catalyst is at most 1 mol. A larger amount thereof is wasteful.

The addition of the catalyst can be conducted by adding it as a solution. For example, in place of adding hydrochloric acid, it can be added in a solution of anhydrous methanol. In the same manner as hydrochloric acid, tetramethyl-ammonium hydroxide can be used in an aqueous solution or an ethanol solution.

When the composition comprising one or more organometallic compounds represented by the general formulae (1) and (2), the organic solvent, water and, if necessary, the catalyst, is subjected to the reaction at a suitable reaction temperature for a suitable reaction time and, if necessary, under suitable stirring conditions, the hydrolysis and polycondensation reaction occur to form a polymer or viscosity of the liquid composition is increased to form a sol.

The sol thus formed is polymerized to form a gel, which is then heated to 400° to 1,000° C. to form a glass. This process is well-known as sol-gel process.

It is also well known that when the glass-forming reaction is conducted on another support, an oxide film can be formed thereon.

The process of the present invention is conducted for the purpose of bonding the inorganic polymer having the metal-oxygen-metal bond in the sol, with the metal surface to be treated, thereby fixing the organic reactive group (bonded with the inorganic polymer through a covalent bond) on the metal surface. The formation of a layer of another compound or substance on the metal surface is not the purpose of the present invention.

After the sol or liquid composition is applied to the metal surface, it is dried with air by heating. As a result, the inorganic polymer comprising the metal-oxygen-metal bond is gelled and simultaneously closely adhered to the metal surface. The drying is conducted in order to evaporate the solvent, remaining water and, in some cases, the catalyst. The drying step can be omitted depending on the use of the treated support. Alternatively, heating can be used for the purpose of enhancing the close contact between the inorganic polymer in the present liquid composition and the metal surface to be treated. In this case, the drying step can be continued after the solvent and water are completely vaporized. The maximum drying temperature must be lower than the decomposition temperature of the organic functional group [A in the formula (1)] on the metal surface. Usually, a temperature ranges room temperature to 200° C., preferably room temperature to 150° C.

The variety, shape and the surface conditions of the metal to be treated by the process of the present invention are not particularly limited. The metal may be a pure metal such as aluminum, iron, copper, titanium or zirconium, or an alloy of them.

The shape of the metal substrate may be a plate, pipe, wire or the like.

The liquid composition (sol) usable in the present invention can be applied to the metal surface by brushing, dipping, atomizing, spin coating, doctor blade coating or the like. The application method is suitably selected depending on the shape of the metal surface and intended thickness of the coating film.

Although the metal surface is preferably clean and is not stained with oil or the like, it can be coated without any cleaning step, unless it is severely stained with oil or the like. If necessary, the metal surface can be mechanically roughened or roughened by electrolytic deposition or electrolytic etching.

The process of the present invention can be employed for the treatment of a metal surface having an oxide film naturally formed or a metal surface oxidized by anodic oxidation or catalytic oxidation. As a matter of course, a metal surface having another oxide film formed thereon by flame spraying, painting or CVD method can be also treated.

A metal surface having another surface layer formed thereon by, for example, treatment with a silicate or nitriding treatment can also be treated by the process of the present invention.

The liquid composition usable in the present invention is prepared by reacting a composition comprising one or more organometallic compounds of the general formula (1), the organic solvent, water and, if necessary, an organometallic compound of the general formula (2) and the catalyst, at a suitable reaction temperature, for a suitable reaction time and, if necessary, under suitable stirring conditions. The liquid composition is not particularly limited so far as the hydrolysis and polycondensation reaction have proceeded therein sufficiently for the adhesion of the inorganic polymer with the metal surface to fix the organic functional group thereon.

Those skilled in the art know whether the object of the present invention can be attained or not with the liquid composition as follows: the liquid composition is practically applied to the metal surface, the presence of the functional group on the surface is confirmed from reflective infrared absorption spectrum or Raman spectrum. The adhesion of the inorganic polymer layer to the metal surface is determined by a tape peeling test after drying.

The degree of progress of the hydrolysis and polycondensation reactions can be estimated by a spectroscopic method. The degree of progress of the hydrolysis reaction is known from, for example, infrared absorption spectral method wherein as the reaction proceeds, vibrational absorption spectrum due to —OR in the general formula (1) is weakened and that due to —OH is strengthened. The progress of the subsequent polycondensation reaction can be known from, for example, the fact that a vibrational absorption spectrum due to the metal-oxygen-metal bond appears and gradually becomes stronger in the IR absorption spectrum. In NMR spectrum, it is found that the width of the spectrum due to A of the general formula (1) is widened as the polycondensation reaction proceeds. The progress of the reaction can be confirmed also from this fact.

When one of these spectral data is confirmed, the liquid composition is usable for attaining the object of the present invention.

In an easier method, the viscosity of the liquid composition is monitored immediately after the preparation thereof and, when the viscosity is significantly increased after initiation of the reaction, it is indicated that the liquid composition has been prepared.

The preferred viscosity which varies depending on the composition and reaction conditions ranges from 0.2 cP to 10 P at the time of the preparation of the liquid composition. When the viscosity is too low, it is difficult to monitor the progress of the polymerization and, on the contrary, when it is too high, it cannot be easily applied to the metal and, in some cases, the coating film is peeled off after drying.

The liquid composition can be used by diluting it with a suitable solvent or liquid like water when it is coated on the metal surface to be treated. Alternatively, the liquid composition can be concentrated by evaporating a part of the solvent used when it has been prepared. The viscosity of the liquid composition at the time of coating may vary depending on the kind of a coating process or a coating thickness, but the viscosity of 0.2 cP to 10 P is very useful.

The viscosity can be determined from the molecular weight of the inorganic polymer in the liquid composition. In this case, the reaction is stopped by trimethylsilylating treatment, the liquid composition thus obtained is dissolved in benzene and the number-average molecular weight is determined by cryoscopic method. The results should be 1000 to tens of thousands.

The metal surface treated by the process of the present invention has an intended quantity of an intended functional group to exhibit various chemical functions.

Generally, the surface free energy $\gamma$ of a substance can be classified into a dispersion force energy $\gamma^d$ and polar energy $\gamma^p$. To maximize the interaction between different substances and thereby obtaining a high adhesion, the values $\gamma^d$ and $\gamma^p$ of one of them are made close to those of the other. Since $\gamma^d$ and $\gamma^p$ of the metal surface treated by the process of the present invention can be adjusted by varying the variety and relative amount of A of the organometallic compound of the general formula (1), they are desirably adjusted suitably to $\gamma^d$ and $\gamma^p$ of a coating material to be applied to the surface thereof, in order to obtain an excellent adhesion.

When the heat-reactive organic functional group is fixed on the metal surface according to the present invention and when a coating film having a group reactive with the organic functional group is formed on the metal surface and heated, only the heated area thereof is chemically and firmly adhered to the metal surface.

When the functional group A of the general formula (1) is photo-reactive, the photo-induced adhesion effect can be obtained between the metal surface treated by the process of the present invention and the other photosensitive material.

When the functional group to be fixed on the metal surface is an ordinary radical-polymerizable group, a monomer or oligomer polymerizable or copolymerizable with it is applied to the metal surface together with an initiator and an external stimulation suitable for the variety of the initiator is given thereto to form a chemical bond between the surface and the coating film. As a matter of course, it is heated when the initiator is a heat-induced polymerization initiator or it is irradiated with a light when it is a photo-induced polymerization initiator. When such an external, imagewise irradiation is conducted, a latent image (chemical bonds) is formed between the metal surface and the coating film.

Since an intended functional group can be fixed on the metal surface treated by the process of the present invention, any substance having a group chemically reactive with the functional group can be adhered thereto. In other words, when some substance is to be adhered to a support, it is sufficient that an organometallic compound of the general formula (1) having an organic functional group A reactive with a reactive group of this substance (or a reactive group introduced into the substance) is selected and a liquid composition containing it is formed. The metal surface is treated with this liquid composition and then the above substance is applied thereon to conduct the intended chemical reaction.

The process of the present invention can be used in wide applications. For example, it is used for providing a functional group suitable for the purpose of forming composite materials firmly adhered through a covalent bond, in the formation of a weather-resistant coating film on a construction material, immobilization of a functional chemical substance such as an enzyme, and application of a functional compound to a pipe material or the like.

As a matter of course, according to the process of the present invention, not only adhesion, but also releasability, surface slip characteristics and surface friction can be altered as desired.

The functional chemical substances applicable to the metal surface thus treated include a photosensitive resin layer of a presensitized lithographic plate (PS plate).

The compositions for forming the photosensitive resin layers include any composition having a solubility or swelling properties in a developer, which property can be changed by the exposure. Typical examples of them include as follows:

(1) Photosensitive resin layer comprising a diazo resin and a binder:

Preferred negative working photosensitive diazo compounds include diphenylamine-p-diazonium salt-/formaldehyde condensate (so-called photosensitive diazo resin) which is a reaction product of a diazonium salt and an organic condensing agent having a reactive carbonyl group such as an aldol or acetal as described in U.S. Pat. Nos. 2,063,631 and 2,667,415. Other condensed diazo compounds usable herein are described in Japanese Patent Publication for Opposition Purpose (J. P. KOKOKU) Nos. 49-48001, 49-45322 and 49-45323. These types of the photosensitive diazo compounds are usually in the form of a water-soluble inorganic salt thereof and, therefore, they can be applied in the form of an aqueous solution thereof to the metal surface. Further, these water-soluble diazo compounds can be reacted with an aromatic or aliphatic compound having one or more phenolic hydroxyl groups, sulfonic acid groups or both of them by a process described in J. P. KOKOKU No. 47-1167 and the resulting, substantially water-insoluble photosensitive diazo resin can be used.

Further, reaction products of them with a hexafluorophosphoric acid salt or tetrafluoroboric acid salt can be used as described in Japanese Patent Unexamined Published Application (J. P. KOKAI) No. 56-121031.

Examples of the reactants having a phenolic hydroxyl group include hydroxybenzophenone, 4,4-bis(4'-hydroxyphenyl)-pentanoic acid, resorcinol and diphenolic acids such as diresorcinol. They may have a substitutent. The hydroxybenzophenones include 2,4-dihydroxybenzophenone, 2-hydroxy-4-methoxybenzophenone, 2,2'-dihydroxy-4,4'-dimethoxybenzophenone or 2,2',4,4'-tetrahydroxybenzophenone. Preferred sulfonic acids include aromatic sulfonic acids such as benzene-, toluene-, xylene-, naphthalene-, phenol-, naphthol- and benzophenonesulfonic acids and soluble salts of them such as ammonium and alkali metal salts. The sulfonic acid group-containing compounds may be usually substituted with a lower alkyl group, a nitro group, a halogen atom and/or another sulfonic acid group. Preferred examples of them include benzenesulfonic acid, toluenesulfonic acid, dodecylbenzenesulfonic acid, naphthalenesulfonic acid, 2,5-dimethylbenzenesulfonic acid, sodium mesitylenesulfonate, naphthalene-2-sulfonic acid, 1-napthol-2(or 4)-sulfonic acid, 2,4-dinitro-1-naphthol-7-sulfonic acid, 2-hydroxy-4-methoxy-benzophenone-5-sulfonic acid, sodium m-(p'-anilinophenylazo)-benzenesulfonate, alizarinsulfonic acid, o-toluidine-m-sulfonic acid, ethanesulfonic acid and ammonium salts and alkali metal salts of them. Alcohol sulfonic esters and salts of them are also usable. These compounds are easily available on the market as anionic surfactants. These salts include, for example, ammonium and alkali metal salts of lauryl sulfate, alkylaryl sulfates, p-nonylphenyl sulfate, 2-phenylethyl sulfate and isooctylphenoxydiethoxyethyl sulfate.

The substantially water-insoluble photosensitive diazo resins are isolated as a precipitate by mixing a water-soluble photosensitive diazo resin with an aqueous solution of the above-described aromatic or aliphatic compound in substantially equal amounts.

The diazo resins described in British Patent No. 1,312,925 are also preferred. Further, the diazo resins as described in J. P. KOKAI Noes. Hei 1-102456, 1-102457, 1-254949, 1-255246 and 2-66 can be used.

The most preferred diazo resins are 2-methoxy-4-hydroxy-5-benzoylbenzenesulfonic acid salt, hexafluorophosphoric acid salt and dodecylbenzenesulfonic acid salt of a condensate of p-diazodiphenylamine and formaldehyde.

The suitable amount of the diazo resin in the photosensitive resin layer is 3 to 50%, preferably 5 to 20% by weight. When the amount of the diazo resin is reduced, storability is reduced, although the photosensitivity is increased as a matter of course. The most preferred amount of the diazo resin is about 8 to 20% by weight.

Various polymeric compounds are usable as a binder. In the present invention, those having a hydroxy, amino, carboxylic acid, amido, sulfonamido, active methylene, thioalcohol or epoxy group are preferred. The preferred binders include shellac as described in British Patent No. 1,350,521, polymers comprising hydroxyethyl acrylate units or hydroxyethyl methacrylate units as a main recurring units as described in British Patent No. 1,460,978 and U.S. Pat. No. 4,123,276, polyamide resin as described in U.S. Pat. No. 3,751,257, phenolic resin and polyvinyl acetal resins such as polyvinyl formal resin and polyvinyl butyral resin as described in British Patent No. 1,074,392, a linear polyurethane resin as described in U.S. Pat. No. 3,660,097, as well as polyvinyl alcohol phthalate resin, epoxy resin produced by condensing bisphenol A with epichlorohydrin, polymers having an amino group such as polyaminostyrene and polyalkylamino (meth)acrylates, and cellulose derivatives such as cellulose acetate, cellulose alkyl ethers and cellulose acetate phthalate.

Also, the polymeric compounds as described in J. P. KOKAI Noes. Sho 54-98614, 61-267042, 62-58242, 61-128123, 63-123452, 62-123453, and 63-113450 can be used.

The compositions comprising the diazo resin and the binder may further contain a pH indicator as described in British Patent No. 1,041,463, and additives such as phosphoric acid and dyes described in U.S. Pat. No. 3,236,646.

(2) Photosensitive resin layer comprising an o-quinone diazide compound:

Particularly preferred o-quinone diazide compounds are o-naphthoquinone diazide compounds as described in U.S. Pat. Nos. 2,766,118, 2,767,092, 2,772,972, 2,859,112, 2,907,665, 3,046,110, 3,046,111, 3,046,115, 3,046,118, 3,046,119, 3,046,120, 3,046,121, 3,046,122, 3,046,123, 3,061,430, 3,102,809, 3,106,465, 3,635,709 and 3,647,443, and many other publications. Among them, particularly preferred are o-naphthoquinone diazido sulfonic acid esters or o-naphthoquinone diazido carboxylic acid esters of aromatic hydroxyl compounds, and o-naphthoquinone diazido sulfonic acid amides and o-naphthoquinone diazido carboxylic acid amides of aromatic amino compounds. Particularly preferred are compounds produced by esterification reaction of pyrogallol/acetone condensate with o-naphthoquinone diazidosulfonic acid as described in U.S. Pat. No. 3,635,709, compounds produced by esterification reaction of a polyester having a terminal hydroxyl group with o-naphthoquinone diazido sulfonic acid or o-naphthoquinone diazido carboxylic acid as described in U.S. Pat. No. 4,028,111, compounds produced by esterification reaction of p-hydroxystyrene homopolymer or a copolymer thereof with another copolymerizable monomer with o-naphthoquinone diazido sulfonic acid or o-naphthoquinone diazido carboxylic acid as described in British Patent No. 1,494,043, and compounds produced by amidation reaction of a copolymer of p-aminostyrene with a copolymerizable monomer with o-naphthoquinone diazido sulfonic acid or o-naphthoquinone diazido carboxylic acid as described in U.S. Pat. No. 3,759,711.

Although these o-quinone diazido compounds can be used singly, it is preferably used in the form of a mixture thereof with an alkali-soluble resin. The preferred alkali-soluble resins include novolak-type phenolic resins such as phenol-formaldehyde resin, o-cresol-formaldehyde resin and m-cresol-formaldehyde resin. It is more preferred that the above-described phenolic resin is used in combination with a condensate of phenol or cresol substituted with an alkyl group having 3 to 8 carbon atoms with formaldehyde such as t-butylphenol/formaldehyde resin as described in British Patent No. 4,123,279. The amount of the alkali-soluble resin contained in the photosensitive resin layer is about 50 to 85% by weight, preferably 60 to 80% by weight, based on the total composition constituting the photosensitive resin layer.

The photosensitive composition comprising the o-quinone diazide compound may further contain, if necessary, a dye, a plasticizer and an additive capable of imparting printing-out properties to the composition as described in British Patent Nos. 1,401,463 and 1,039,475 and U.S. Pat. No. 3,969,118.

(3) Photosensitive resin layer comprising an azide compound and a binder (polymeric compound):

This layer comprises, for example, a composition comprising an azide compound and a water-soluble or alkali-soluble polymeric compound as described in British Patent Nos. 1,235,281 and 1,495,861 and J. P. KOKAI Nos. 51-32331 and 51-36128 or a composition comprising a polymer having an azido group and a polymeric compound as a binder as described in J. P. KOKAI Nos. 50-5102, 50-84302, 50-84303 and 53-12984. Also, the composition comprising polyvinylacetal resin containing an azido group, as described in J. P. KOKOKU No. 49-44601 and J. P. KOKAI Noes. 52-89914 and 59-208552, can be used.

(4) Photopolymerizable photopolymer resin layers:

The representative example of these resin layers is a photosensitive composition comprising an ethylenically unsaturated addition-polymerizable compound, a polymeric compound which is soluble in an organic solvent and has a film-forming property, and a photoinitiator. This composition is specifically explained in J. P. KOKAI No. 61-282836.

(5) Photocrosslinkable photopolymer resin layers:

For example, the polyester compounds as described in J. P. KOKAI No. 52-96696 and the polyvinylcinnamate resins as described in British Patent Nos. 1,112,277, 1,313,390, 1,341,004 and 1,377,747 are included in this kind of resin layer. Particularly preferable composition is those comprising a photocrosslinkable polymer having a maleimide group at a side chain. This composition is specifically explained in J. P. KOKAI No. 62-78544.

(6) Other photosensitive resin layers:

These layers comprise, for example, a polyester compound as described in J. P. KOKAI No. 52-96696, polyvinyl cinnamate resin as described in British Patent Nos. 1,112,277, 1,313,390, 1,341,004 and 1,377,747, a photocrosslinkable polymer having a maleimido group at its side chain as described in U.S. Pat. Nos. 4,079,041 and 4,416,975, and a photo-polymerizable photopolymer composition as described in U.S. Pat. Nos. 4,072,528, 4,072,527, 4,511,645 and 4,687,727.

(7) Electrophotographic photosensitive resin layer:

Electrophotographic photosensitive resins mainly comprise a photoconductive compound and a binder. They can contain, if necessary, a known pigment, dye, chemical sensitizer and other additives in order to improve the sensitivity or to obtain a desired photosensitive wave length region. The photosensitive resin layer may comprise a single layer or plural layers each having a function of generating an electric charge or that of transporting it. A lithographic plate can be prepared by forming a toner image on the photosensitive resin layer by a known electrophotographic process to obtain a resist layer and decorating a non-image area. The lithographic plates are described in J. P. KOKOKU Nos. 37-17162 and 38-6961, J. P. KOKAI Nos. 56-107246 and 60-254142, J. P. KOKOKU Nos. 59-36259 and 59-25217, J. P. KOKAI Nos. 56-146145, 62-194257, 57-147656, 58-100862 and 57-161863 and many other publications. They are preferred.

The thickness of the photosensitive resin layer is 0.1 to 30 $\mu$m, preferably 0.5 to 10 $\mu$m.

The amount of the photosensitive resin layer formed on the metal surface is about 0.1 to 7 $g/m^2$, preferably 0.5 to 4 $g/m^2$.

The detailed description will be made on the compatibility of the adhesion with the peelability with reference to a PS plate.

An aluminum plate degreased by an ordinary method is used as a support. If necessary, the surface of the plate may be roughened with a brush or treatment with an electric current. Also, if necessary, an oxide film layer may be formed on the surface by anodic oxidation method and further, if necessary, it may be immersed in No. 3 sodium silicate bath to form a silicate layer on the surface thereof.

The aluminum plate is treated with the liquid composition of the present invention prepared from the organometallic compound of the general formula (1) having a radical-polymerizable group as the group A. The plate is then coated with a radical-polymerizable photosensitive composition to form a layer. It is imagewise exposed to light to cause imagewise interfacial photoadhesion. The composition was removed from the unexposed area with a developer to leave the imagewise photopolymerized film adhered to the aluminum plate. An ink and water are applied thereto. The ink adheres to the photopolymerized, adherent area and water adheres to the unexposed area. This plate is used as a printing plate.

When an excess organic functional group is present in the unexposed area to which water is to be applied, the ink also adhered thereto in addition to water, to stain the prints. This phenomenon can be prevented by fixing many OH groups and the functional groups A on the metal support surface to intensify its hydrophilic properties or by converting the functional group A into a hydrophilic group such as an alcoholic group, taking advantage of the reactivity of the group A.

The number of OH groups on the metal surface can be increased by converting A of the organometallic compound of the general formula (1) into OH and/or by using a large amount of the organometallic compound of the general formula (2). The OR group of the organometallic compound of the general formula (2) is converted into an OH group by the hydrolysis. Although most of the OH groups thus formed is used for forming the metal-oxygen-metal bond, the balance remains as an OH group on the surface.

Thus, the ink repellency of the unexposed area and affinity thereof for water can be increased by suitable selection of the functional group A and by suitable combination of the organometallic compounds of the general formulae (1) and (2).

The present invention will be described in detail with reference to a case wherein the organometallic compound of the general formula (1) having a $CH_2=CH-$ group as an organic functional group A is used, the surface of an aluminum plate is treated with the liquid composition of the present invention and a photosensitive composition is applied thereto to form a PS plate.

$Si(OC_2H_5)_4$ and $CH_2=CHSi(OCOCH_3)_3$ are placed in a beaker. Acetic acid is added thereto as a catalyst and then water is added thereto as a hydrolyzing agent.

Ethanol is added to the mixture as a solvent and the resultant mixture is stirred at room temperature to form a homogeneous solution.

The solution is transported into a three-necked flask provided with a stirrer and a reflux condenser and the flask is immersed in an oil bath at room temperature. The bath temperature is elevated to 80° to 90° C. under stirring.

As the reaction proceeds, the viscosity of the solution is increased. Supposedly, the following reactions occur in the solution:

(Hydrolysis reaction)

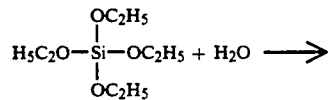

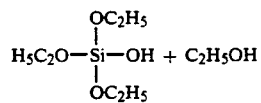

(Polycondensation reaction)

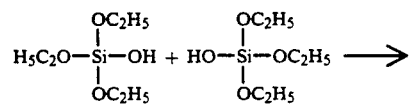

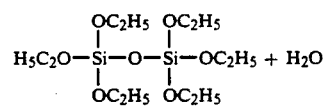

(Hydrolysis reaction)

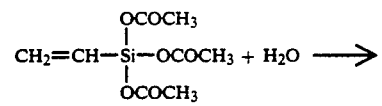

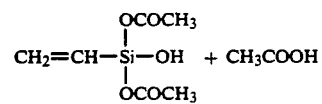

(Heteropolycondensation reaction)

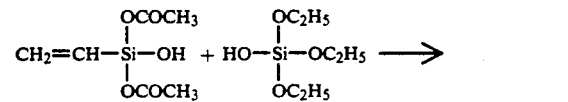

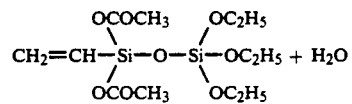

Although in the above formulae, the polycondensate grows in one of the four directions with respect to the four functional groups bonded to Si, practically the condensed chains grow in plural directions. Further, heteropolycondensation reaction of the compounds different from each other occurs in addition to the homopoly-condensation reaction. Thus, the reactions cannot be perfectly represented by the reaction formulae.

After the hydrolysis and polycondensation reaction proceed to some extent, it is considered that polymers of the following formula are present in the solution:

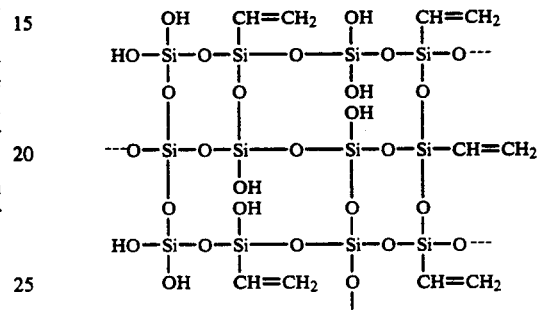

Practically, various compounds having various Si—O—Si chain lengths and functional group contents are formed. The average chemical structure of them is nearly as follows:

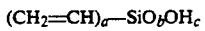

wherein $b+\frac{1}{2}(a+c)$ is 2.

Although $-OC_2H_5$ and $-OCOCH_3$ groups would be present in the course of the reaction, they are not shown herein. The values of a, b and c in the above formula vary depending on various experimental parameters such as the composition of the organosilicon compounds as feed materials, amount of water, variety and amount of the solvent, variety and amount of the catalyst, reaction temperature and reaction time. Therefore, the final product having desired values of a, b and c can be obtained by adjusting these conditions.

The liquid composition thus obtained is applied to the metal surface.

It is known that an oxide film is slightly present on the metal surface and some OH groups are present in its surface, unless the metal surface is clean under ultrahigh vacuum. When the liquid composition is applied to the metal surface, parts of the compound rotate which have a degree of freedom around a single bond near Si, the compound in the solution being fixed on the metal surface with its highly inorganic part facing to the metal surface side. Supposedly, this phenomenon occurs due to the interaction between the oxide on the metal surface or OH groups on the surface and Si—O—Si network in the liquid composition or silanol group.

When the liquid composition applied to the surface is heated, the solvent and catalyst residue can be rapidly volatilized. Supposedly, the formation of the chemical bond between the metal surface and the inorganic polymer in the liquid composition is accelerated by heat. Although the mechanism of the formation of the bond has not been fully elucidated, supposedly, it is mainly due to dehydration condensation between the OH group of the metal surface and the OH group of the inorganic polymer.

The surface-treated metal support thus obtained in this case has vinyl groups and hydroxyl groups supposedly protruding outward on the metal surface.

A photo-polymerizable photosensitive resin layer is formed on the thus treated metal surface to form a PS plate. The resin preferably comprises a monomer having a >C=C< double bond.

Polymerizable monomers and binders having a terminal allyl group (—CH$_2$CH=CH$_2$) or acrylate group

(—OCCH=CH$_2$)

are easily available on the market. A mixture of them with a photo-radical forming agent at a suitable ratio is applied to the metal surface on which vinyl groups are fixed, and then dried to form a PS plate.

The PS plate is then imagewise exposed. The polymerization of the vinyl group occurs in the exposed area to solidify the photosensitive layer and simultaneously to form a covalent bond between the photosensitive layer and the metal surface. Namely, the vinyl polymerized photosensitive layer forms a new covalent bond the vinyl group fixed on the metal surface through a covalent bond and therefore the layer firmly adheres to the metal surface to form a firm layer.

On the other hand, in the unexposed area, no polymerization of the photosensitive layer occurs and no bond is formed between the photosensitive layer and the metal surface. Therefore, the photosensitive layer in only the unexposed area is dissolved by immersion in a suitable developer.

As a result, the exposed resion layer is firmly adhered to the support to form the vinyl polymer film, while the support surface in the unexposed region is uncoated and has OH groups and vinyl groups protruding on the surface.

In order to use the plate thus formed as a printing plate, the vinyl polymer layer must accept ink and the uncovered non-image area of the metal surface must accept water so as to make an ON/OFF as an image. There is substantially no problem on the vinyl polymer film area in respect of an ink receptivity, because both of them are lipophilic. The non-image area must be sufficiently hydrophilic in order to spread water on it and to repel the ink. Thus, the balance between the OH groups and the vinyl groups on the metal surface is important.

When the density of the OH groups on the surface is sufficiently high, the uncovered metal surface obtained by the process of the present invention can serve as the non-image area.

When the density of OH groups on the surface is low and the density of the vinyl groups becomes relatively high and, therefore, the lipophilic property becomes important, the hydrophilic treatment of the vinyl groups is necessitated.

This treatment can be conducted by a method wherein a sulfate ion is bonded with the vinyl group by means of a coordination bond and then it is hydrolyzed into a corresponding alcohol or a method wherein an Si—C bond is oxidatively cut into a silanol.

It will be easily understood that the process of the present invention can be employed in various ways, since the composition is closely adhered to the metal surface by means of a functional group fixed on the metal surface in the image area and the reaction for making it hydrophilic is conducted in the non-image area.

The following examples will further illustrate the present invention.

EXAMPLE 1

23.4 g of triacetoxyvinylsilane, 1 g of acetic acid and 3.6 g of ion-exchanged water were placed in a 100 ml beaker. 50 g of ethanol were added thereto and the mixture was stirred at room temperature for 5 min.

The whole solution thus obtained was transferred into a three-necked flask, which was provided with a reflux condenser and immersed in an oil bath at room temperature. The temperature of the solution in the flask was elevated to 80° C. in about 30 min while the solution was stirred with a magnetic stirrer.

30 min after the elevation of the bath temperature to 80° C., pieces of the aluminum plate having roughened surface were immersed in the reaction mixture for 5 sec and dried. The diffuse reflection IR spectrum of them was determined. The formation of the Si—O—Si bond and the presence of the surface vinyl groups and surface silanol groups were confirmed. It was thus proved that the solution could be used as a liquid composition for treating the metal surface.

Even 10 hr after the elevation of the bath temperature to 80° C., the solution was able to be used for treating the metal surface. However, after 11 hr, the solution became too viscous and the rotation of the magnetic stirrer was reduced to about 1 rps. When the metal surface was coated with the liquid composition by its immersion therein, rough streaks were formed on the coating film unfavorably. However, when a drop of the liquid composition was applied to the metal surface and spread on it by rolling a glass rod thereon, an even coating film was formed.

When the liquid composition was further kept in the bath at 80° C., it was entirely gelled after 12 hr. The pot life of the liquid composition in this Example was about 11 hr at 80° C.

EXAMPLE 2

23.4 g of triacetoxyvinylsilane, 3.6 g of ion-exchanged water and 50 g of ethanol were placed in a 100 ml beaker and the mixture was stirred at room temperature for 5 min.

The whole solution thus obtained was transferred into a three-necked flask and the hydrolysis and polycondensation reaction were conducted under the same conditions as those of Example 1.

30 min after the elevation of the bath temperature to 80° C., pieces of the aluminum plate having roughened surface were immersed in the reaction mixture for 5 sec and dried. The diffuse reflection IR spectrum of them was determined. The formation of the Si—O—Si bond and the presence of the surface vinyl groups and surface silanol groups were confirmed. However, the absorbance intensity was about ⅓ of that of Example 1 after the equal reaction time. The fact that no IR peak due to acetoxy group was utterly detected indicated that the hydrolysis had been completed then. Although the degree of polycondensation was slightly lower than that of Example 1, it could be used as a solution for treating the metal surface at that time.

Even 10 hr after the elevation of the bath temperature to 80° C., the solution was able to be used for treating the metal surface. However, after 11 hr, the solution was unsuitable for coating due to the formation of streaks on the coating film surface unfavorably, but it was able to be used for roll coating.

Even 22 hr after the elevation of the bath temperature to 80° C., the liquid composition was not gelled and it was able to be applied to the metal surface by roll-coating to form an even coating film.

After 50 ml of ethanol were added thereto and the mixture was stirred, a homogeneous liquid composition having a reduced viscosity was able to be obtained again. It could be used for a dip coating.

The liquid composition was taken out of the bath and its pot life was examined. No gelation occurred and no precipitate was formed even after keeping it at room temperature for one year.

In NMR spectrum obtained three days after the preparation of the liquid composition, a signal due to an acetoxy group observed as the maximum peak of the starting triacetoxyvinylsilane was not observed at all in the liquid composition. The signal due to a vinyl group was broader than that of the starting material and it was sifted by 0.3 ppm towards the peak of tetra-methylsilane added as an internal standard. These results indicated that the electron-attractive acetoxy group around the silicon atom, with which a vinyl group was bonded by means of a covalent bond, had been completely removed and that the movability of the vinyl group was reduced because of the formation of the inorganic polymer containing a silicon atom.

The liquid composition thus prepared was used for treating an aluminum plate having a roughened surface, an aluminum plate further having a film formed by anodic oxidation and an aluminum plate further having a silicate layer formed by treatment with No. 3 sodium silicate on the film formed by the anodic oxidation. The diffuse reflection IR spectrum of each of them was determined. No significant difference in the quantities of the vinyl groups fixed on the surface was able to be found among the three plates. The liquid composition was able to be used for treating a silicone wafer and a copper plate in the same manner as above. The properties of the liquid composition were unchanged after storage at room temperature for one year.

EXAMPLE 3 AND COMPARATIVE EXAMPLE 1

50 g of $CH_2=CHSi(OCOCH_3)_3$, 1.1 g of acetic acid, 7.7 g of distilled water and 100 g of ethanol were placed in a beaker and the mixture was stirred at room temperature to obtain a homogeneous solution. The solution was transferred into a three-necked flask provided with a stirrer and a reflux condenser. The flask was immersed in an oil bath and the reaction was conducted under stirring for 7 hr while the bath temperature was kept at 80° C. to prepare a liquid composition (sol)(1).

Separately, an aluminum plate having a thickness of 0.3 mm was degreased with an alkali and subjected to anodic oxidation in a 7% aqueous sulfuric acid solution to obtain a support having a thickness of 2.0 $g/m^2$.

The sol (1) was applied to the support in an amount of 10 $mg/m^2$ (on dry basis) with a whirler and dried at 170° C. for 10 min.

The following liquid composition 1 for forming a photosensitive resin layer was applied, with a whirler to the aluminum support having the organic functional group ($CH_2=CH-$) on the surface and then dried at 100° C. for 2 min, to prepare a photosensitive lithographic plate A1. The quantity of the film after drying was 1.5 $g/m^2$.

| Liquid composition 1 for forming photosensitive resin layer: | |
|---|---|
| Trimethylolpropane triacrylate | 15 g |
| Poly(allyl methacrylate/methacrylic acid) copolymer in a molar ratio of 80/20 | 50 g |
| 2,4-Trichloromethyl-(4'-methoxynaphthyl)-S-triazine | 1.5 g |
| Propylene glycol monomethyl ether | 1500 g |
| F-177 (a fluorine-containing surfactant mfd. by Dainippon Ink & Chemicals, Inc.) | 1 g |
| Oil-soluble dye (Victoria Pure Blue BOH) | 1.5 g |

A photosensitive lithographic plate B1 was prepared in the same manner as described above except that the sol (1) was omitted.

After sufficiently vacuumizing, the photosensitive lithographic plates A1 and B1 were exposed with PS Light of Fuji Photo Film Co., Ltd. at a distance of 1 m for 3 min. Then they were kept under various conditions as shown in Table 1 below and subjected to a tape peeling test to give the results shown in Table 1. It is apparent from the results that the adhesion of the photosensitive resin layer to the support of the photosensitive lithographic plate (A1), to which the sol (1) had been applied, was far superior to that of the photosensitive lithographic plate (B1).

TABLE 1

| | | Immediately after exposure | Exposure and dipping in water for 3 days | Exposure and dipping in water for 7 days | Exposure, dipping in water for 3 days and boiling for 7 hours |
|---|---|---|---|---|---|
| Example 3 | Photsensitive lithographic plate A1 | Not peeled | Not peeled | Not peeled | Not peeled |
| Comparative Example 1 | Photosensitive lithographic plate B1 | Not peeled | Not peeled | Partially peeled under 1 $kg/cm^2$ | Partially peeled under 100 $g/cm^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 4 AND COMPARATIVE EXAMPLE 2

Example 3 was repeated except that 57.4 g of Si-$(OC_2H_5)_4$, 4.6 g of $CH_2=CHSi(OCOCH_3)_3$, 7.2 g of water, 100 g of ethanol, and 2 g of acetic acid were used as starting materials, to give a liquid composition (sol)(2).

Using the sol(2), Example 3 was repeated except that the coating amount of the sol(2) (on dry basis) was 1 $mg/m^2$, to give a photosensitive lithographic plate A2.

The procedure was repeated without using the sol(2), to give a photosensitive lithographic material B2.

These plates A2 and B2 were exposed and subjected to a tape peeling test in the same manner as Example 3. The results are shown in Table 3 below.

It is apparent from the results that the adhesion of the photosensitive resin layer to the support of the plate A2 was much superior to that of the plate B2.

It is apparent from the results that the adhesion of photosensitive resin layer to the support of the plate A3 was much superior to that of the plate B3.

TABLE 2

|  |  | Immediately after exposure | Exposure and dipping in water for 3 days | Exposure and dipping in water for 7 days | Exposure, dipping in water for 3 days and boiling for 7 hours |
| --- | --- | --- | --- | --- | --- |
| Example 4 | Photsensitive lithographic plate A2 | Not peeled | Not peeled | Not peeled | Not peeled |
| Comparative Example 2 | Photosensitive lithographic plate B2 | Not peeled | Not peeled | Partially peeled under 1 kg/cm$^2$ | Partially peeled under 100 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

TABLE 3

|  |  | Immediately after exposure | Exposure and dipping in water for 3 days | Exposure and dipping in water for 7 days | Exposure, dipping in water for 3 days and boiling for 7 hours |
| --- | --- | --- | --- | --- | --- |
| Example 5 | Photsensitive lithographic plate A3 | Not peeled | Not peeled | Not peeled | Not peeled |
| Comparative Example 3 | Photosensitive lithographic plate B3 | Not peeled | Not peeled | Partially peeled under 1 kg/cm$^2$ | Partially peeled under 100 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 5 AND COMPARATIVE EXAMPLE 3

Example 4 was repeated except that $Si(OC_2H_5)_4$ (57.4 g),

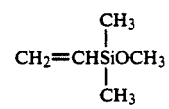

(2.3 g), water (14.4 g), ethanol (100 g) and acetic acid (2 g) were used as starting materials, to give sol(3).

The sol(3) was applied to the support used in Example 4 and dried in the same manner as Example 4, to prepare an aluminum support having an organic functional group ($CH_3$ and $CH_2=CH-$) on the surface.

The photosensitive resin layer composition used in Example 4 was applied to the resultant support, to prepare a photosensitive lithographic plate A3 in the same manner as Example 4.

The same procedure was repeated without using the sol(3), to prepare a photosensitive lithographic plate B3.

These plates A3 and B3 were exposed and subjected to a tape peeling test in the same manner as Example 4. The results are shown in Table 3 below.

EXAMPLE 6 AND COMPARATIVE EXAMPLE 4

Example 5 was repeated except that $CH=CHCH_2Si(OC_2H_5)_3$ (4.1 g) was used in place of

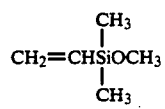

(2.3 g), to prepare sol(4).

The sol(4) was applied to the support used in Example 4 and dried in the same manner as Example 4, to prepare an aluminum support having an organic functional group ($CH_2=CHCH_2-$) on the surface.

The photosensitive resin layer composition used in Example 4 was applied to the resultant support, to prepare a photosensitive lithographic plate A4 in the same manner as Example 4.

The same procedure was repeated without using the sol(4), to prepare a photosensitive lithographic plate B4.

These plates A4 and B4 were exposed and subjected to a tape peeling test in the same manner as Example 4. The results are shown in Table 5 below.

It is apparent from the result that the adhesion of photosensitive resin layer to the support of the plate A4 was much superior to that of the plate B4.

TABLE 4

|  |  | Immediately after exposure | Exposure and dipping in water for 3 days | Exposure and dipping in water for 7 days | Exposure, dipping in water for 3 days and boiling for 7 hours |
| --- | --- | --- | --- | --- | --- |
| Example 6 | Photsensitive lithographic plate A4 | Not peeled | Not peeled | Not peeled | Not peeled |
| Comparative Example 4 | Photosensitive lithographic | Not peeled | Not peeled | Partially peeled under | Partially peeled under 100 g/cm$^2$ |

TABLE 4-continued

|  | Immediately after exposure | Exposure and dipping in water for 3 days | Exposure and dipping in water for 7 days | Exposure, dipping in water for 3 days and boiling for 7 hours |
|---|---|---|---|---|
| plate B4 |  |  |  | 1 kg/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 7 AND COMPARATIVE EXAMPLE 5

Example 5 was repeated except that

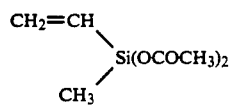

(3.8 g) was used in place of

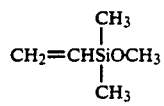

(2.3 g), to prepare sol(5).

The sol(5) was applied to the support used in Example 4 and dried in the same manner as Example 4, to prepare an aluminum support having an organic functional group (CH$_3$—and CH$_2$=CH—) on the surface.

The photosensitive resin layer composition used in Example 4 was applied to the resultant support, to prepare a photosensitive lithographic plate A5 in the same manner as Example 4.

The same procedure was repeated without using the sol(5), to prepare a photosensitive lithographic plate B5.

These plates A5 and B5 were exposed and subjected to a tape peeling test in the same manner as Example 4. The results are shown in Table 5 below.

It is apparent from the results that the adhesion of photosensitive resin layer to the support of the plate A5 was much superior to that of the plate B5.

TABLE 5

|  |  | Immediately after exposure | Exposure and dipping in water for 3 days | Exposure and dipping in water for 7 days | Exposure, dipping in water for 3 days and boiling for 7 hours |
|---|---|---|---|---|---|
| Example 7 | Photsensitive lithographic plate A5 | Not peeled | Not peeled | Not peeled | Not peeled |
| Comparative Example 5 | Photosensitive lithographic plate B5 | Not peeled | Not peeled | Partially peeled under 1 kg/cm$^2$ | Partially peeled under 100 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 8 AND COMPARATIVE EXAMPLE 6

Example 5 was repeated except that CH$_2$=CHCH$_2$NH(CH$_2$)$_3$Si(OCH$_3$)$_3$ (4.4 g) was used in place of

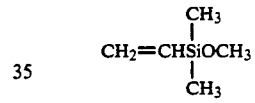

(2.3 g), to prepare sol(6).

The sol(6) was applied to the support used in Example 4 and dried in the same manner as Example 4, to prepare an aluminum support having an organic functional group (CH$_2$=CHCH$_2$NH(CH$_2$)$_3$—) on the surface.

The photosensitive resin layer composition used in Example 4 was applied to the resultant support, to prepare a photosensitive lithographic plate A6 in the same manner as Example 4.

The same procedure was repeated without using the sol(6), to prepare a photosensitive lithographic plate B6.

These plates A6 and B6 were exposed and subjected to a tape peeling test in the same manner as Example 4. The results are shown in Table 6 below.

It is apparent from the result that the adhesion of photosensitive resin layer to the support of the plate A6 was much superior to that of the plate B6.

TABLE 6

|  |  | Immediately after exposure | Exposure and dipping in water for 3 days | Exposure and dipping in water for 7 days | Exposure, dipping in water for 3 days and boiling for 7 hours |
|---|---|---|---|---|---|
| Example 8 | Photsensitive lithographic plate A6 | Not peeled | Not peeled | Not peeled | Not peeled |
| Comparative Example 6 | Photosensitive lithographic plate B6 | Not peeled | Not peeled | Partially peeled under 1 kg/cm$^2$ | Partially peeled under 100 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 9 AND COMPARATIVE EXAMPLE 7

Example 5 was repeated except that

(4.6 g) was used in place of

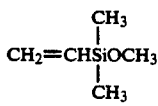

(2.3 g), to prepare sol(7).

The sol(7) was applied to the support used in Example 4 and dried in the same manner as Example 4, to prepare an aluminum support having an organic functional group ($CH_3$—and $CH_2=C(CH_3)COO(CH_2)_3$—) on the surface.

The photosensitive resin layer composition used in Example 4 was applied to the resultant support, to prepare a photosensitive lithographic plate A7 in the same manner as Example 4.

The same procedure was repeated without using the sol(7), to prepare a photosensitive lithographic plate B7.

These plates A7 and B7 were exposed and subjected to a tape peeling test in the same manner as Example 4. The results are shown in Table 7 below.

It is apparent from the result that the adhesion of photosensitive resin layer to the support of the plate A7 was much superior to that of the plate B7.

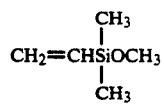

(2.3 g), to prepare sol(8).

The sol(8) was applied to the support used in Example 4 and dried in the same manner as Example 4, to prepare an aluminum support having an organic functional group ($CH_2=CHCOO(CH_2)_3$—) on the surface.

The photosensitive resin layer composition used in Example 4 was applied to the resultant support, to prepare a photosensitive lithographic plate A8 in the same manner as Example 4.

The same procedure was repeated without using the sol(8), to prepare a photosensitive lithographic plate B8.

These plates A8 and B8 were exposed and subjected to a tape peeling test in the same manner as Example 4. The results are shown in Table 8 below.

It is apparent from the result that the adhesion of photosensitive resin layer to the support of the plate A8 was much superior to that of the plate B8.

TABLE 8

| | | Immediately after exposure | Exposure and dipping in water for 3 days | Exposure and dipping in water for 7 days | Exposure, dipping in water for 3 days and boiling for 7 hours |
|---|---|---|---|---|---|
| Example 10 | Photsensitive lithographic plate A8 | Not peeled | Not peeled | Not peeled | Not peeled |
| Comparative Example 8 | Photosensitive lithographic plate B8 | Not peeled | Not peeled | Partially peeled under 1 kg/cm² | Partially peeled under 100 g/cm² |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

TABLE 7

| | | Immediately after exposure | Exposure and dipping in water for 3 days | Exposure and dipping in water for 7 days | Exposure, dipping in water for 3 days and boiling for 7 hours |
|---|---|---|---|---|---|
| Example 9 | Photsensitive lithographic plate A7 | Not peeled | Not peeled | Not peeled | Not peeled |
| Comparative Example 7 | Photosensitive lithographic plate B7 | Not peeled | Not peeled | Partially peeled under 1 kg/cm² | Partially peeled under 100 g/cm² |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 10 AND COMPARATIVE EXAMPLE 8

Example 5 was repeated except that $CH_2=CHCOO(CH_2)_3Si(OCH_3)_3$ (4.6 g) was used in place of

EXAMPLE 11 AND COMPARATIVE EXAMPLE 9

Example 5 was repeated except that $$\begin{array}{c} CH_3 \\ \\ CH_3 \end{array} \diagup\!\!\!\!\!\diagdown \begin{array}{c} O \\ \parallel \\ \\ \parallel \\ O \end{array} N{-}(CH_2)_{10}CONH(CH_2)_3Si(OCH_3)_3$$

(9.4 g) was used in place of $$CH_2=CH\underset{\underset{CH_3}{|}}{\overset{\overset{CH_3}{|}}{Si}}OCH_3$$

(2.3 g), to prepare sol(9).

The sol(9) was applied to the support used in Example 4 and dried in the same manner as Example 4, to prepare an aluminum support having an organic functional group $$CH_3 \underset{\underset{CH_3}{}}{\overset{}{\diagdown}}\!\!\!\!\!\!\!\!\!\!\!\!\underset{\overset{}{\diagup}}{\overset{O}{\overset{\|}{\diagdown}}} N\!\!-\!\!(CH_2)_{10}CONH(CH_2)_3\!-\!$$

on the surface.

The photosensitive resin layer composition used in Example 4 was applied to the resultant support, to prepare a photosensitive lithographic plate A9 in the same manner as Example 4.

The same procedure was repeated without using the sol(9), to prepare a photosensitive lithographic plate B9.

These plates A9 and B9 were exposed and subjected to a tape peeling test in the same manner as Example 4. The results are shown in Table 9 below.

It is apparent from the result that the adhesion of photosensitive resin layer to the support of the plate A9 was much superior to that of the plate B9.

$$CH_2=CH\underset{\underset{CH_3}{|}}{\overset{\overset{CH_3}{|}}{Si}}OCH_3$$

(2.3 g), to prepare sol(10).

The sol(10) was applied to the support used in Example 4 and dried in the same manner as Example 4, to prepare an aluminum support having an organic functional group (CH≡C—) on the surface.

The photosensitive resin layer composition used in Example 4 was applied to the resultant support, to prepare a photosensitive lithographic plate A10 in the same manner as Example 4.

The same procedure was repeated without using the sol(10), to prepare a photosensitive lithographic plate B10.

These plates A10 and B10 were exposed and subjected to a tape peeling test in the same manner as Example 4. The results are shown in Table 10 below.

It is apparent from the result that the adhesion of photosensitive resin layer to the support of the plate A10 was much superior to that of the plate B10.

TABLE 10

|  |  | Immediately after exposure | Exposure and dipping in water for 3 days | Exposure and dipping in water for 7 days | Exposure, dipping in water for 3 days and boiling for 7 hours |
| --- | --- | --- | --- | --- | --- |
| Example 12 | Photosensitive lithographic plate A10 | Not peeled | Not peeled | Not peeled | Not peeled |
| Comparative Example 10 | Photosensitive lithographic plate B10 | Not peeled | Not peeled | Partially peeled under 1 kg/cm$^2$ | Partially peeled under 100 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 13 AND COMPARATIVE EXAMPLE 11

Example 5 was repeated except that CH$_2$=CHSi(OCH$_3$)$_3$ (3.0 g) was used in place of $$CH_2=CH\underset{\underset{CH_3}{|}}{\overset{\overset{CH_3}{|}}{Si}}OCH_3$$

TABLE 9

|  |  | Immediately after exposure | Exposure and dipping in water for 3 days | Exposure and dipping in water for 7 days | Exposure, dipping in water for 3 days and boiling for 7 hours |
| --- | --- | --- | --- | --- | --- |
| Example 11 | Photosensitive lithographic plate A9 | Not peeled | Not peeled | Not peeled | Not peeled |
| Comparative Example 9 | Photosensitive lithographic plate B9 | Not peeled | Not peeled | Partially peeled under 1 kg/cm$^2$ | Partially peeled under 100 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 12 AND COMPARATIVE EXAMPLE 10

Example 5 was repeated except that CH CSi(OC$_2$H$_5$)$_3$(3.8 g) was used in place of (2.3 g), to prepare sol(11).

Separately, the aluminum plate used in Example 4 was anodically oxidized in the same manner as Example 4, was immersed in a 3% sodium silicate solution at 70° C. for 1 min, was washed with water, and then was dried.

The sol(11) was applied to the resultant support and dried in the same manner as Example 4, to prepare an aluminum support having an organic functional group (CH$_2$=CH—) on the surface.

The photosensitive resin layer composition used in Example 4 was applied to the resultant support, to prepare a photosensitive lithographic plate A11 in the same manner as Example 4.

The same procedure was repeated without using the sol(11), to prepare a photosensitive lithographic plate B11.

These plates A11 and B11 were exposed and subjected to a tape peeling test in the same manner as Example 4. The results are shown in Table 11 below.

It is apparent from the result that the adhesion of photosensitive resin layer to the support of the plate A11 was much superior to that of the plate B11.

aluminum support having an organic functional group (CH$_3$— and CH$_2$=CH—) on the surface.

The photosensitive resin layer composition used in Example 4 was applied to the resultant support, to prepare a photosensitive lithographic plate A12 in the same manner as Example 4.

The same procedure was repeated without using the sol(12), to prepare a photosensitive lithographic plate B12.

These plates A12 and B12 were exposed and subjected to a tape peeling test in the same manner as Example 4. The results are shown in Table 12 below.

It is apparent from the result that the adhesion of photosensitive resin layer to the support of the plate A12 was much superior to that of the plate B12.

TABLE 12

| | | Immediately after exposure | Exposure and dipping in water for 3 days | Exposure and dipping in water for 7 days | Exposure, dipping in water for 3 days and boiling for 7 hours |
|---|---|---|---|---|---|
| Example 14 | Photosensitive lithographic plate A12 | Not peeled | Not peeled | Not peeled | Not peeled |
| Comparative Example 12 | Photosensitive lithographic plate B12 | Not peeled | Completely peeled under 10 g/cm$^2$ | Completely peeled under 5 g/cm$^2$ | Completely peeled under 1 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

TABLE 11

| | | Immediately after exposure | Exposure and dipping in water for 3 days | Exposure and dipping in water for 7 days | Exposure, dipping in water for 3 days and boiling for 7 hours |
|---|---|---|---|---|---|
| Example 13 | Photosensitive lithographic plate A11 | Not peeled | Not peeled | Not peeled | Not peeled |
| Comparative Example 11 | Photosensitive lithographic plate B11 | Not peeled | Completely peeled under 10 g/cm$^2$ | Completely peeled under 5 g/cm$^2$ | Completely peeled under 1 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 14 AND COMPARATIVE EXAMPLE 12

Example 5 was repeated except that

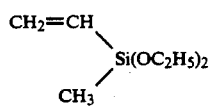

(3.2 g) was used in place of

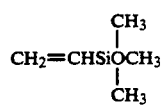

(2.3 g), to prepare sol(12).

Separately, the aluminum plate used in Example 4 was anodically oxidized in the same manner as Example 4, was immersed in a 3% sodium silicate solution at 70° C. for 1 min, was washed with water, and then was dried.

The sol(12) was applied to the resultant support and dried in the same manner as Example 4, to prepare an

EXAMPLE 15 AND COMPARATIVE EXAMPLE 13

Example 5 was repeated except that (CH$_2$=CH)$_2$Si(OC$_2$H$_5$)$_2$ (3.4 g) was used in place of

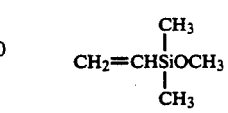

(2.3 g), to prepare sol(13).

Separately, the aluminum plate used in Example 4 was anodically oxidized in the same manner as Example 4, was immersed in a 3% sodium silicate solution at 70° C. for 1 min, was washed with water, and then was dried.

The sol(13) was applied to the resultant support and dried in the same manner as Example 4, to prepare an aluminum support having an organic an aluminum support having an organic functional group (CH$_2$=CH—) on the surface.

The photosensitive resin layer composition used in Example 4 was applied to the resultant support, to prepare a photosensitive lithographic plate A in the same manner as Example 4.

The same procedure was repeated without using the sol(13), to prepare a photosensitive lithographic plate B13.

These plates A13 and B13 were exposed and subjected to a tape peeling test in the same manner as Example 4. The results are shown in Table 13 below.

It is apparent from the result that the adhesion of photosensitive resin layer to the support of the plate A13 was much superior to that of the plate B13.

TABLE 13

|  |  | Immediately after exposure | Exposure and dipping in water for 3 days | Exposure and dipping in water for 7 days | Exposure, dipping in water for 3 days and boiling for 7 hours |
| --- | --- | --- | --- | --- | --- |
| Example 15 | Photosensitive lithographic plate A13 | Not peeled | Not peeled | Not peeled | Not peeled |
| Comparative Example 13 | Photosensitive lithographic plate B13 | Not peeled | Completely peeled under 10 g/cm$^2$ | Completely peeled under 5 g/cm$^2$ | Completely peeled under 1 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 16 AND COMPARATIVE EXAMPLE 14

Example 5 was repeated except that CH$_2$=C(CH$_3$)COO(CH$_2$)$_3$Si(OCH$_3$)$_3$ (5.0 g) was used in place of

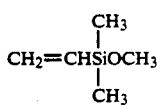

(2.3 g), to prepare sol(14).

Separately, the aluminum plate used in Example 4 was anodically oxidized in the same manner as Example 4, was immersed in a 3% sodium silicate solution at 70° C. for 1 min, was washed with water, and then was dried.

The sol(14) was applied to the resultant support and dried in the same manner as Example 4, to prepare an aluminum support having an organic functional group (CH$_2$=C(CH$_3$)COO(CH$_2$)$_3$—) on the surface.

The photosensitive resin layer composition used in Example 4 was applied to the resultant support, to prepare a photosensitive lithographic plate A14 in the same manner as Example 4.

The same procedure was repeated without using the sol(14), to prepare a photosensitive lithographic plate B14.

These plates A14 and B14 were exposed and subjected to a tape peeling test in the same manner as Example 4. The results are shown in Table 14 below.

It is apparent from the result that the adhesion of photosensitive resin layer to the support of the plate A14 was much superior to that of the plate B14.

TABLE 14

|  |  | Immediately after exposure | Exposure and dipping in water for 3 days | Exposure and dipping in water for 7 days | Exposure, dipping in water for 3 days and boiling for 7 hours |
| --- | --- | --- | --- | --- | --- |
| Example 16 | Photosensitive lithographic plate A14 | Not peeled | Not peeled | Not peeled | Not peeled |
| Comparative Example 14 | Photosensitive lithographic plate B14 | Not peeled | Completely peeled under 10 g/cm$^2$ | Completely peeled under 5 g/cm$^2$ | Completely peeled under 1 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 17 AND COMPARATIVE EXAMPLE 15

Example 5 was repeated except that

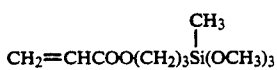

(4.4 g) was used in place of

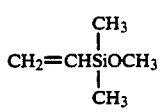

(2.3 g), to prepare sol(15).

Separately, the aluminum plate used in Example 4 was anodically oxidized in the same manner as Example 4, was immersed in a 3% sodium silicate solution at 70° C. for 1 min, was washed with water, and then was dried.

The sol(15) was applied to the resultant support and dried in the same manner as Example 4, to prepare an aluminum support having an organic functional group (CH$_3$— and CH$_2$=CHCOO(CH$_2$)$_3$—) on the surface.

The photosensitive resin layer composition used in Example 4 was applied to the resultant support, to prepare a photosensitive lithographic plate A in the same manner as Example 4.

The same procedure was repeated without using the sol(15), to prepare a photosensitive lithographic plate B15.

These plates A15 and B15 were exposed and subjected to a tape peeling test in the same manner as Example 4. The results are shown in Table 15 below.

It is apparent from the result that the adhesion of photosensitive resin layer to the support of the plate A15 was much superior to that of the plate B15.

TABLE 15

| | | Immediately after exposure | Exposure and dipping in water for 3 days | Exposure and dipping in water for 7 days | Exposure, dipping in water for 3 days and boiling for 7 hours |
|---|---|---|---|---|---|
| Example 17 | Photosensitive lithographic plate A15 | Not peeled | Not peeled | Not peeled | Not peeled |
| Comparative Example 15 | Photosensitive lithographic plate B15 | Not peeled | Completely peeled under 10 g/cm$^2$ | Completely peeled under 5 g/cm$^2$ | Completely peeled under 1 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 18 AND COMPARATIVE EXAMPLE 16

Example 5 was repeated except that

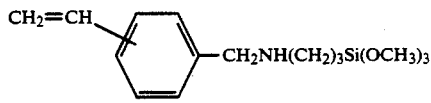

(6.0 g) was used in place of $$CH_2=CH\underset{\underset{CH_3}{|}}{\overset{\overset{CH_3}{|}}{Si}}OCH_3$$

(2.3 g), to prepare sol(16).

Separately, the aluminum plate used in Example 4 was anodically oxidized in the same manner as Example 4, was immersed in a 3% sodium silicate solution at 70° C. for 1 min, was washed with water, and then was dried.

The sol(16) was applied to the resultant support and dried in the same manner as Example 4, to prepare an aluminum support having an organic functional group

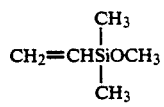

on the surface.

The photosensitive resin layer composition used in Example 4 was applied to the resultant support, to prepare a photosensitive lithographic plate A16 in the same manner as Example 4.

The same procedure was repeated without using the sol(16), to prepare a photosensitive lithographic plate B16.

These plates A16 and B16 were exposed and subjected to a tape peeling test in the same manner as Example 4. The results are shown in Table 16 below.

It is apparent from the result that the adhesion of photosensitive resin layer to the support of the plate A16 was much superior to that of the plate B16.

TABLE 16

| | | Immediately after exposure | Exposure and dipping in water for 3 days | Exposure and dipping in water for 7 days | Exposure, dipping in water for 3 days and boiling for 7 hours |
|---|---|---|---|---|---|
| Example 18 | Photosensitive lithographic plate A16 | Not peeled | Not peeled | Not peeled | Not peeled |
| Comparative Example 16 | Photosensitive lithographic plate B16 | Not peeled | Completely peeled under 10 g/cm$^2$ | Completely peeled under 5 g/cm$^2$ | Completely peeled under 1 g/cm$^2$ |

Note) In the tape peeling test, and adhesive tape having a width of 10 mm was applied to the coated surface, then the tape was peeled at an angle of 180° at a velocity of 20 mm/min and the force necessitated for the peeling was determined with a strain gauge.

EXAMPLE 19 AND COMPARATIVE EXAMPLE 17

A sol(17) prepared from a mixture of the following composition in the same manner as that of Example 3 except that the reaction temperature and the reaction time were 70° C. and 8 hr, respectively:

| | |
|---|---|
| Si(OCOCH$_3$)$_4$ | 39.6 g |
| HSCH$_2$Si(OCOCH$_3$)$_3$ | 12.6 g |
| Acetic acid | 0.6 g |
| Distilled water | 7.2 g |
| Ethanol | 100 g |

On the other hand, the surface of an aluminum plate having a thickness of 0.3 mm was grained with a nylon brush and an aqueous suspension of 400 mesh pumice powder, and then thoroughly washed with water. It was etched by immersion in a 10% aqueous sodium hydroxide solution at 70° C. for 60 sec, washed with running water and neutralized by washing with 20% nitric acid. The surface of the plate was roughened by electrolysis by an electrochemical surface-roughening method described in J.P. KOKAI No. 53-67507 wherein the electrolysis was conducted by using sinusoidal alternating current having V$_A$ of 12.7 V and V$_C$ of 9.1 V and quantity of anode time electricity of 160 C/dm$^2$ in a 1% aqueous nitric acid solution. It was then immersed in 30% aqueous sulfuric acid, desmatted at 55° C. for 2 min and anodically oxidized in 7% aqueous sulfuric acid to obtain a thickness of 2.0 g/m$^2$. It was then immersed in a 3% aqueous sodium silicate solution at 70° C. for 1 min, washed with water and dried.

The sol(17) was applied to the resultant support and then dried in the same manner as that of Example 3. The following liquid composition 2 for forming a photosensitive resin layer was applied to the resulting aluminum support with a whirler and then it was dried at 80° C. for 2 min to prepare a photosensitive lithographic plate C.

| Liquid composition 2 for forming photosensitive resin layer: | |
| --- | --- |
| 4-Dizaodiphenylamine/formaldehyde | 1.0 g |
| condensate hexafluorophosphate | |
| Polymer (a) | 5.0 g |
| Malic acid | 0.05 g |
| FC-430 (a fluorine-containing surfactant mfd. by 3M Co. in U.S.A.) | 0.05 g |
| Oil-soluble dye (Victoria Pure Blue BOH) | 0.1 g |
| 2-Methoxyethanol | 60 g |
| Methanol | 20 g |
| Methyl ethyl ketone | 20 g |

(Note)
Polymer (a) was vinyl copolymer and, more particularly, a 2-hydroxyethyl methacrylate copolymer. To prepare the copolymer, 300 g of dioxane was heated in a stream of nitrogen gas at 100° C. and a mixture of 150 g of 2-hydroxyethyl methacrylate, 60 g of acrylonitrile, 79.5 g of methylmethacrylate, 10.5 g of methacrylic acid and 1.2 g of benzoyl peroxide was dropped therein over 2 hours. Fifteen minutes after completion of the dropping there was added to the reaction mixture 300 g of dioxane and 0.3 g of benzoyl peroxide and the resulting mixture maintained under the reaction conditions for an additonal four hours. After completion of the reaction, the reaction mixture was diluted with methanol and poured into water to precipitate the copolymer form. The precipitate was dried at 70° C. in vacuo to obtain a 2-hydroxyethyl methacrylate copolymer (I) having an acid value of 20.

A photosensitive lithographic plate D was prepared in the same manner as above except that sol (17) was omitted.

The photosensitive lithographic plates C and D were imagewise exposed with PS Light of Fuji Photo Film Co., Ltd. through a negative film at a distance of 1 m for 1 min. Then they were immersed in a mixture of DN-3C (an aqueous alkali developer of Fuji Photo Film Co., Ltd.) and tap water in a volume ratio of 1:1 for 5 min. The surface of the photosensitive resin layer in the image area was lightly rubbed with a nail. The lithographic plate D was easily scarred, although the lithographic plate C was hardly scarred.

The lithographic plates C and D were imagewise exposed in the same manner as that described above and then developed with the same developer as above and a mixture of Gum Solution FN-2 (a product of Fuji Photo Film Co., Ltd.) with tap water in a volume ratio of 1:1 by means of PS-800H (automatic developing machine of Fuji Photo Film Co., Ltd.). Then it was subjected to a printing test with a Heidelberg GTO printing machine. 100,000 prints were produced with the lithographic plate C, while only 80,000 prints were produced with the lithographic plate D. The non-image area of neither lithographic plate C nor D was scummed.

EXAMPLE 20~26 AND COMPARATIVE EXAMPLE 18

Sols (18)~(24) were prepared from the mixtures listed in the following Table 17 in the same manner as that of Example 3.

TABLE 17

| | Example No. | | | | | | |
| --- | --- | --- | --- | --- | --- | --- | --- |
| | 20 | 21 | 22 | 23 | 24 | 25 | 26 |
| | | | | Sol. No. | | | |
| Sol. Composition | (18) | (19) | (20) | (21) | (22) | (23) | (24) |
| CH$_2$=CHSi(OCOCH$_3$)$_3$ | 11.6 | | | | | | |
| CH$_2$=CHSi(OC$_2$H$_5$)$_3$ | | 11.6 | 11.6 | 11.6 | 11.6 | 11.6 | 11.6 |
| Si(OCOCH$_3$)$_4$ | 39.6 | | | | | | |
| Si(OC$_2$H$_5$)$_4$ | | 31.2 | 31.2 | 28.1 | 28.1 | 31.2 | 31.2 |
| Ti(OC$_2$H$_5$)$_4$ | | | | | 3.4 | | |
| Al[OCH(CH$_3$)$_2$]$_3$ | | | | | | 3.1 | |
| CH$_3$COOH | 0.6 | 0.6 | 0.6 | 0.6 | 0.6 | | |
| HCl | | | | | | 0.4 | |
| Tetramethyl ammonium hydride | | | | | | | 1.0 |
| Distilled water | 7.2 | 7.2 | 7.2 | 7.2 | 7.2 | 7.2 | 7.2 |
| Ethanol | 100 | 100 | 90 | 100 | 100 | 100 | 100 |
| Ethyleneglycol | | | 10 | | | | |
| Photosensitive Lithographic Plate No. | E1 | E2 | E3 | E4 | E5 | E6 | E7 |

These sols (18)~(24) were applied to the same support as used in Example 19 and then dried in the same manner as that of Example 3. The following liquid composition for forming a photosensitive resin layer was applied to the resultant supports and dried in the same manner as Example 19 to prepare photosensitive lithographic plates E1~7.

| Liquid composition 3 for forming photosensitive resin layer: | |
| --- | --- |
| Trimethylolpropane triacrylate | 20 g |
| Poly(allyl methacrylate/methacrylic acid) copolymer in a molar ratio of 80/20 | 50 g |
| 2,4-Trichloromethyl-(4'-methoxynaphthyl)-S-triazine | 2 g |
| Behenic acid amide | 1 g |
| Propylene glycol monomethyl ether | 1500 g |
| F-177 (a fluorine-containing Surfactant mfd. by Dainippon Ink & Chemicals, Inc.) | 1.5 g |
| Oil-soluble dye (Victoria Pure Blue BOH) | 1.5 g |

A photosensitive lithographic plate F was prepared in the same manner as above except that the sol (18) was omitted.

The photosensitive lithographic plates E1 and E2 and F were imagewise exposed, developed and subjected to the printing test in the same manner as that of Example 19. 220,000 prints were produced with the lithographic plates E1 and 2, while 180,000 prints were produced with F.

The plates E1~E7 and F were subjected to a tape peeling test in the same manner as Example 3. The results show that the plate F was partially peeled under 200 g/cm$^2$ for three days in water after the exposure and then in boiled water for 7 hours, while the plates E1~E7 were not peeled at all.

EXAMPLE 27 AND COMPARATIVE EXAMPLE 19

A sol (25) was prepared from a mixture of the following composition in the same manner as that of Example 3.

| | |
|---|---|
| $CH_2=CH-Si(OCOCH_3)_3$ | 11.6 g |
| $Si(OCOCH_3)_4$ | 39.6 g |
| Acetic acid | 0.6 g |
| Distilled water | 7.2 g |
| Ethanol | 100 g |

The sol (25) was applied to the same support as that used in Example 19 except that the treatment with the aqueous sodium silicate solution was omitted and dried in the same manner as that of Example 3. The following liquid composition for forming a photosensitive resin layer was applied to the support and dried in the same manner as that of Example 19 to prepare a photosensitive lithographic plate G.

The amount of the photosensitive resin layer was 1 g/m² (on dry basis).

| Liquid composition 4 for forming photosensitive resin layer: | |
|---|---|
| N-[2-(Methacryloyloxy)ethyl]-2,3-dimethyl-maleimide/methacrylic acid copolymer in a weight ratio of 65/35 | 5 g |
| Photosensitizer of the following structural formula: | 0.25 g |

$$H_3C \text{—} \underset{\underset{S}{\big|}}{\bigcirc} \text{—} \overset{\overset{O}{\|}}{C} \text{—} \bigcirc \text{—} COOC_2H_5$$

| | |
|---|---|
| Propylene glycol monomethyl ether | 80 g |
| Methyl ethyl ketone | 80 g |
| Megafac F-177 (a fluorine-containing nonionic surfactat mfd. by Dainippon Ink and Chemicals, Inc.) | 0.03 g |
| Copper phthalocyanine pigment (CL Pigment Blue 15) in 10% dispersion of plasticizer | 1.0 g |

The procedure was repeated without using sol(25) to prepare a photosensitive lithographic plates H.

The photosensitive lithographic plates G and H were exposed in the same manner as that of Example 19 and then developed with a mixture of DP-4 (aqueous alkali developer mfd. by Fuji Photo Film Co., Ltd.) and tap water in a volume ratio of 1:7 and a mixture of a gum solution FP (mfd. by Fuji Photo Film Co., Ltd.) with tap water in a volume ratio of 1:1, in the same manner as that of Example 19. The lithographic plate G was not scarred and had an excellent image, while the lithographic plate H was slightly scarred in the image area in the course of the development.

The lithographic plates G and H were subjected to the printing test in the same manner as that of Example 19. 60,000 prints were produced with the lithographic plate G, while only 40,000 prints were produced with the lithographic plate H.

EXAMPLES 28 TO 32 AND COMPARATIVE EXAMPLE 20

Sols (26)~(30) were prepared from the mixtures listed in the following table 18 in the same manner as Example 3.

TABLE 18

| Example No. | 28 | 29 | 30 | 31 | 32 |
|---|---|---|---|---|---|
| Sol No. | (26) | (27) | (28) | (29) | (30) |
| Sol Composition | | | | | |
| $CH_2=C(CH_3)COO(CH_2)_3Si(OCH_3)_3$ | 2.5 | 2.5 | 2.5 | 2.5 | 0.2 |
| $Si(OC_2H_5)_3$ | 18.7 | 18.7 | 18.7 | 18.7 | 18.7 |
| $H_2O$ | 7.2 | 72 | 720 | 7.2 | 7.2 |
| $CH_3COOH$ | 1.0 | 1.0 | 1.0 | 1.0 | 1.0 |
| Ethanol | 50 | 50 | 50 | 45 | 45 |
| Propyleneglycol | | | | 5 | 5 |
| Photosensitive Lithographic Plate No. | I1 | I2 | I3 | I4 | I5 |

The sols(26)~(30) were applied to the support used in Example 27 and then dried in the same manner as Example 3. Then, the photosensitive resin layer composition used in Example 27 was applied to each of the resultant supports and dried in the same manner as Example 27 so that the coating amount (on dry basis) was 1.5 g/m², to prepare photosensitive lithographic plates I1 to I5.

The same procedure was repeated without using the sols, to prepare a photosensitive lithographic plate J.

The plate I1 and J were subjected to the printing test in the same manner as Example 27. 50,000 prints were produced with the plate J, while 100,000 prints were produced with the plate I1.

Further, the plates I1 to I5 and J were subjected to a tape peeling test in the same manner as Example 3. The results show that the plate J was peeled under 100 g/cm² in water for 3 days after the exposure and then in boiled water for 7 hours, while the plates I1 to I5 were not peeled at all.

EXAMPLE 33 AND COMPARATIVE EXAMPLE 21

A sol (31) was prepared from a mixture of the following composition in the same manner as that of Example 1 except that the reaction temperature and reaction time were changed to 70° C. and 8 hr, respectively.

| | |
|---|---|
| $CH_2=CH-Si(OCOCH_3)_3$ | 7.0 g |
| $HSCH_2Si(OCOCH_3)_3$ | 7.6 g |
| $Si(OCOCH_3)_4$ | 37.0 g |
| Acetic acid | 0.6 g |
| Distilled water | 7.2 g |
| Ethanol | 100 g |

The support as that used in Example 19 was immersed in the sol(31) and then dried. The following liquid composition 5 for forming a photosensitive resin layer was applied to the resultant aluminum support and then dried in the same manner as that of Example 19, to prepare a lithographic plate K.

The amount of the photosensitive resin layer was 2.0 g/m² (on dry basis).

| Liquid composition 5 for forming photosensitive resin layer: | |
|---|---|
| β-Cinnamoyloxyethyl methacrylate/methacrylic acid copolymer (weight ratio: 90/10) (acid value: 61, molecular | 5 g |

43
-continued

Liquid composition 5 for forming photosensitive resin layer:
weight determined according to GPC: 48,000)

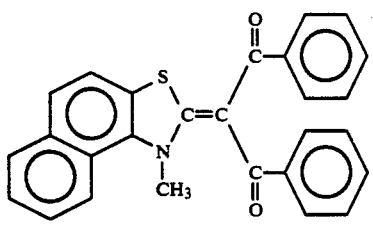 0.2 g

| | |
|---|---|
| PF<sub>6</sub> salt of p-diazodiphenylamine/-formaldehyde condensate | 0.2 g |
| Diethyl phthalate | 0.5 g |
| F-177 (a fluorine-containing nonionic surfactant mfd. by Dainippon Ink & Chemicals, Inc.) | 0.02 g |
| Methyl ethyl ketone | 30 g |
| Ethylene glycol monomethyl ether | 10 g |
| Propylene glycol monomethyl ether | 55 g |
| Ion-exchanged water | 5 g |

A photosensitive lighographic plate L was prepared in the same manner as above except that the sol (31) was omitted.

These photosensitive lithographic plates were exposed, developed and subjected to the printing test in the same manner as that of Example 19. 300,000 prints were produced with the lithographic plate K, while only 250,000 prints were produced with the lithographic plate L.

What is claimed is:

1. A process for treating a metal surface comprising providing a liquid composition comprising an inorganic polymer produced by hydrolyzing and then polycondensing an organometallic compound having an organic functional group and a group capable of being hydrolyzed and then polycondensed in an organic solvent under conditions such that said organic functional group is kept unreacted and applying said liquid composition under conditions such that said inorganic polymer is adhered to the metal surface and said organic functional group is kept unreacted and remains on the metal surface.

2. The process of claim 1 wherein said organometallic compound is represented by the general formula:

$$A_mM(OR)_n$$

wherein
A represents an organic functional group,
M represents a metal,
R represents a hydrogen atom or an alkyl group, or a functional group which can be replaced with an alkyl group in an organic solvent, and
m and n each represents a positive integer satisfying $1 \leq m+n \leq 6$ and when m is two or more, A's may be the same as or different from each other.

3. The process of claim 2 wherein said functional group A is selected from the group consisting of a hydrogen atom, a hydroxy group; an alkyl group substituted with a substituent other than an unsubstituted aryl; an aryl group substituted with a substituent other than an unsubstituted alkyl; a substituted or unsubstituted propargyl group; a substituted or unsubstituted alkoxy group; a silyl group; and a siloxy group.

4. The process of claim 3 wherein a substitutent on the substituted alkyl, aryl, alkenyl, propargyl or alkoxy group is selected from the group consisting of a halogen atom, an alkyl group, an aryl group, a hydroxy group, an alkoxy group, an aryloxy group, an acyloxy group, a carbamoyloxy group, an alkoxycarbonyloxy group, an acyl group, an alkoxycaronyl group, a carbamoyl group, a carboxy group, a propargyl group, an amino group, an alkylamino group, an acylamino group, a ureido group, a carbamate group, a diazonio group, a diazo group, an azo group, a mercapto group, an alkylthio group, a sulfonyl group, a sulfo group, a cyano group, an isocyanate group, a thiocyanate group, a sulfamoyl group, a nitro group, a silyl group and a siloxy group.

5. The process of claim 3 wherein said functional group A is selected from the group consisting of H—, HO—, CH<sub>2</sub>Cl—, CF<sub>3</sub>—(CF<sub>2</sub>—)<sub>3</sub>, HOCH<sub>2</sub>CH<sub>2</sub>CH<sub>2</sub>—

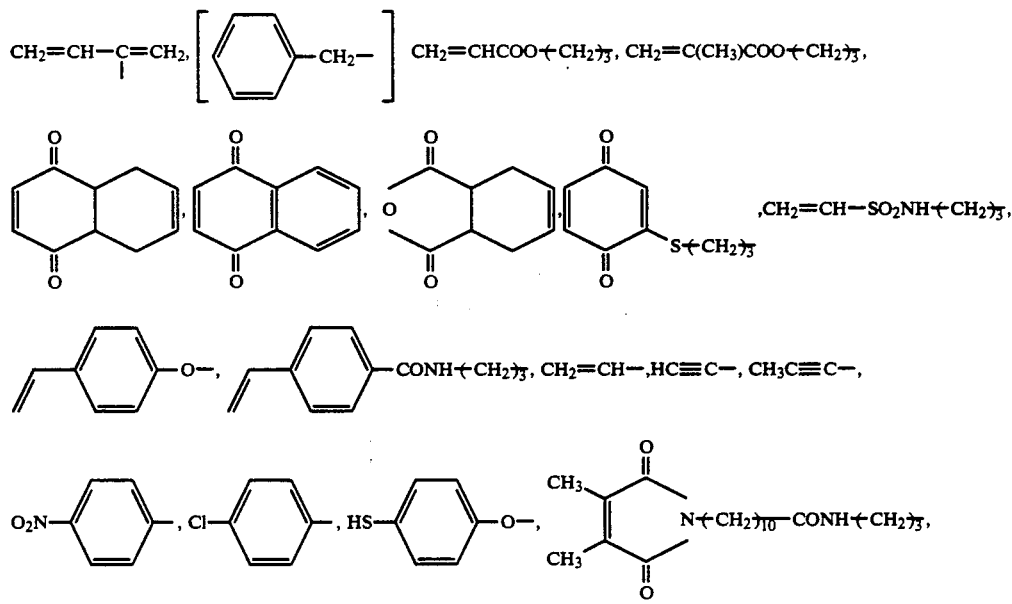

-continued
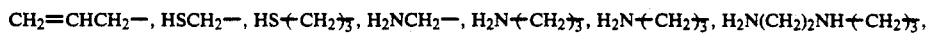
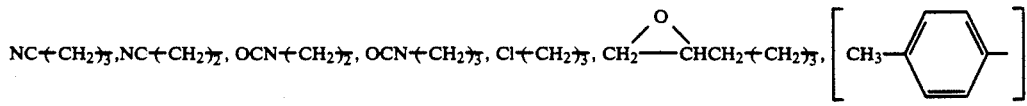
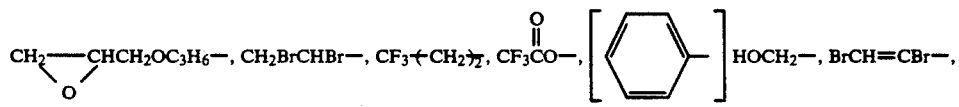
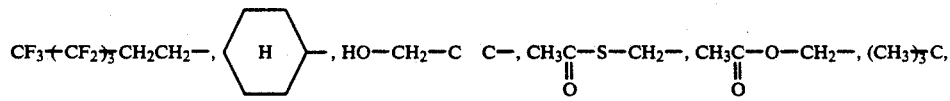
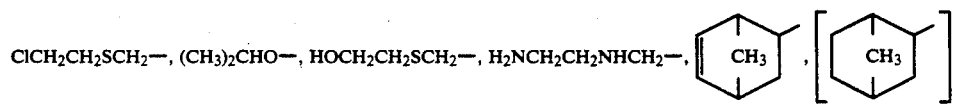
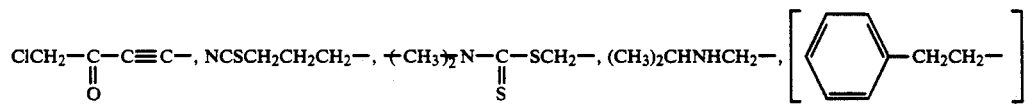
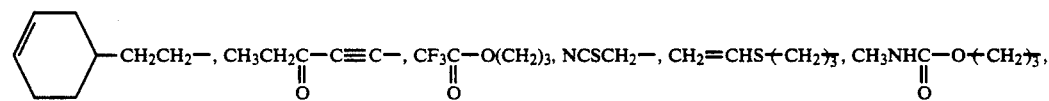
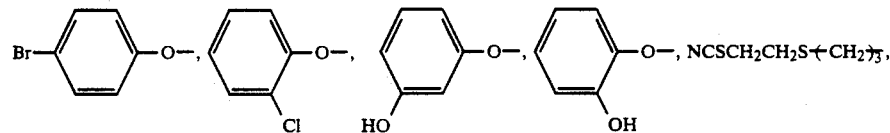
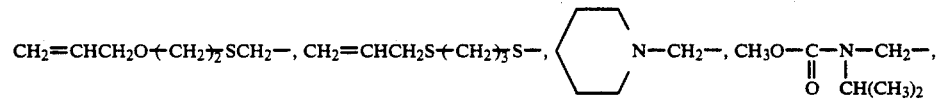
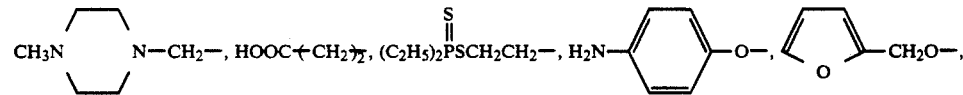
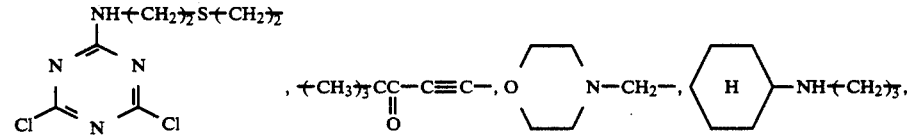
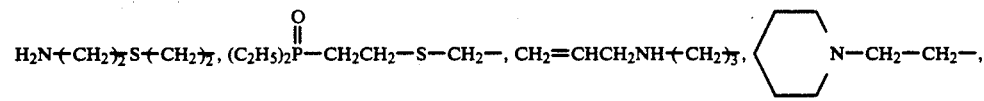
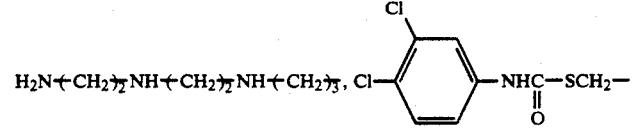

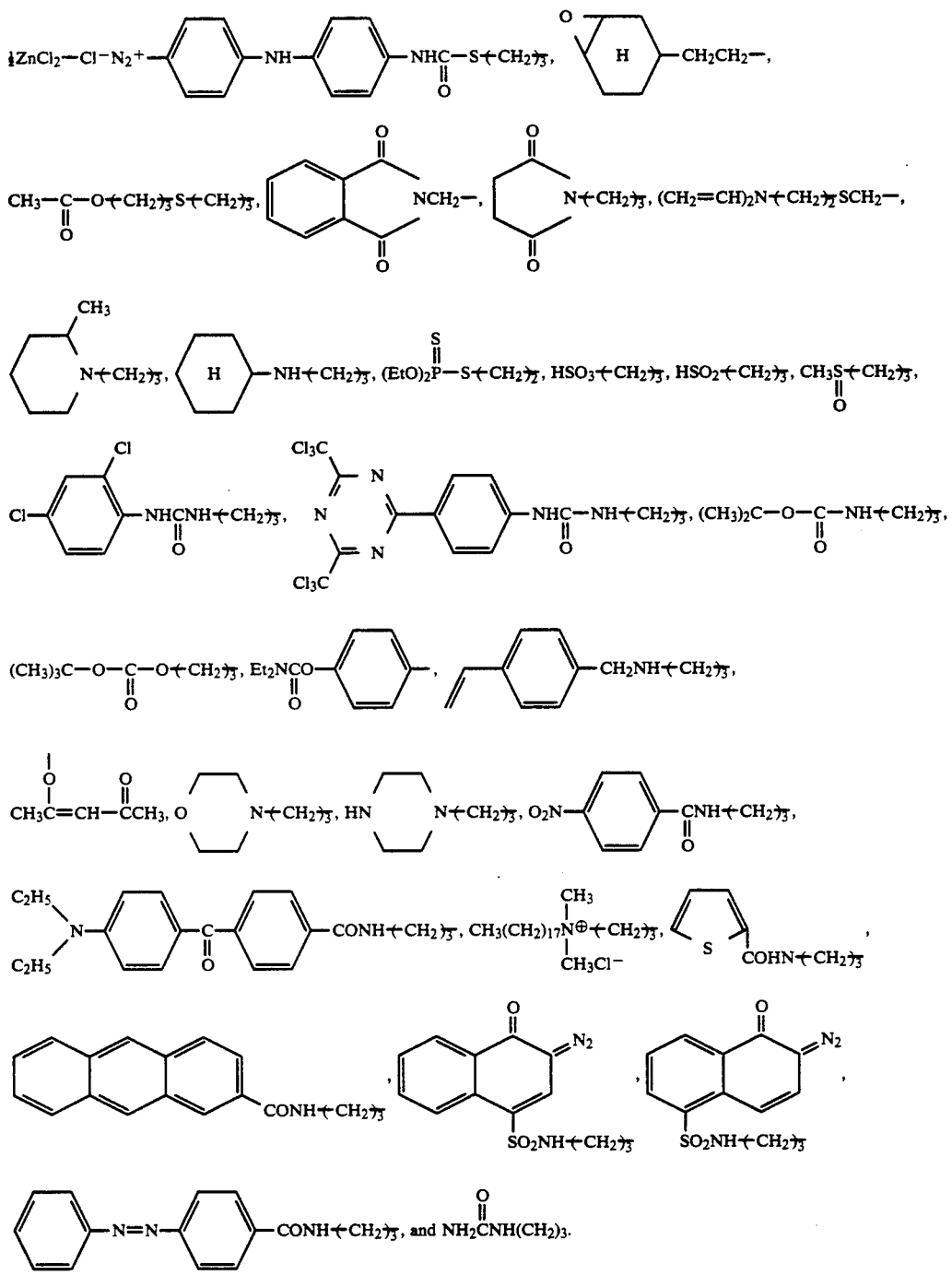

6. The process of claim 2 wherein said M is selected from the group consisting of Li, Na, K, Rb, Cs, Be, Mg, Ca, Sr, Ba, Sc, Y, rare earth metals, Ti, V, Cr, Mn, Fe, Co, Ni, Cu, Zn, Zr, Nb, Mo, Hf, Ta, W, Ru, Rh, Pd, Ir, Pt, B, Al, Ga, In, Tl, Si, Ge, Sn, Pb, P, As, Sb and Bi.

7. The process of claim 6 wherein said M is Al, Si or Ti.

8. The process of claim 2 wherein said alkyl group as said R is selected from the group consisting of $CH_3-$, $C_2H_5-$, $n-C_3H_7-$, $i-C_3H_7-$, $n-C_4H_9-$, $sec-C_4H_9-$, $tert-C_4H_9-$ or a cyclohexyl group.

9. The process of claim 1 wherein said organometallic compound is used together with a compound having the following general formula:

$M(OR)_n$ wherein

M is a metal,

R is a hydrogen atom or an alkyl group, or a functional group which can be replaced with an alkyl group in an organic solvent, and n is a positive integer satisfying $1 \leq n \leq 6$.

10. The process of claim 1 wherein said organometallic compound is selected from the group consisting of
H$_2$N(CH$_2$)$_2$NH(CH$_2$)$_3$—Si(OCH$_3$)$_3$,
CH$_2$=CH—Si(OCOCH$_3$)$_3$, CH$_2$=CH—Si(OC$_2$H$_5$)$_3$,
H$_2$N(CH$_2$)$_3$—Si(OC$_2$H$_5$)$_3$, OCNCH$_2$CH$_2$CH$_2$—Si(OCH$_3$)$_3$, $$\underset{\underset{H}{|}}{CH_3Si(OCH_3)_2},$$

HSi(OCH$_3$)$_2$,

CH$_2$ClSi(OCH$_3$)$_3$,

CH$_3$Si(OCH$_3$)$_3$,

HSCH$_2$Si(OCH$_3$)$_3$, $$CH_2=CH\underset{\underset{CH_3}{|}}{\overset{\overset{CH_3}{|}}{Si}}OCH_3,$$

CH$_2$=CHSi(OCH$_3$)$_3$,

CH$_2$=CHCH$_2$Si(OC$_2$H$_5$)$_3$,

HSCH$_2$CH$_2$Si(OCH$_3$)$_3$, $$\underset{CH_3}{\overset{CH_2=CH}{\diagdown}}Si(OCOCH_3)_2,$$

$$\underset{CH_3}{\overset{CH_2=CH}{\diagdown}}Si(OC_2H_5)_2,$$

(CH$_2$=CH)$_2$Si(OC$_2$H$_5$)$_2$, $$H_2N(CH_2)_3\underset{\underset{CH_3}{|}}{Si}(OC_2H_5)_2,$$

$$H_2N(CH_2)_2NH(CH_2)_3\underset{\underset{CH_3}{|}}{Si}(OCH_3)_2,$$

NC(CH$_2$)$_2$Si(OC$_2$H$_5$)$_3$, $$\underset{O}{\underset{\diagdown\diagup}{CH_2\text{---}CHCH_2OC_3H_6Si(OCH_3)_3}},$$

CH$_2$=CHCH$_2$NH(CH$_2$)$_3$Si(OCH$_3$)$_3$, $$(C_2H_5O)_2\overset{\overset{S}{\|}}{P}S(CH_2)_2Si(OCH_3)_2,$$

CH$_2$=C(CH$_3$)COO(CH$_2$)$_3$Si(OCH$_3$)$_3$, $$CH_2=C(CH_3)COO(CH_2)_3\underset{\underset{CH_3}{|}}{Si}(OCH_3)_2,$$

CH$_2$=CHCOO(CH$_2$)$_3$Si(OCH$_3$)$_3$, $$CH_2=CHCOO(CH_2)_3\underset{\underset{CH_3}{|}}{Si}(OCH_3)_2,$$

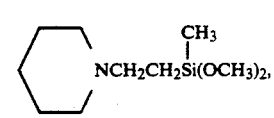
NCH$_2$CH$_2$Si(OCH$_3$)$_2$,

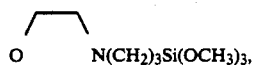
N(CH$_2$)$_3$Si(OCH$_3$)$_3$,

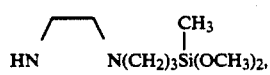
N(CH$_2$)$_3$Si(OCH$_3$)$_2$,

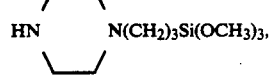
N(CH$_2$)$_3$Si(OCH$_3$)$_3$, $$\overset{\overset{O}{\|}}{NH_2CHN(CH_2)_3Si(OC_2H_5)_3},$$

$$\underset{O}{\underset{\diagdown\diagup}{CH_2\text{---}CHCH_2O(CH_2)_3}}\underset{\underset{CH_3}{|}}{Si}(OC_2H_5)_2,$$

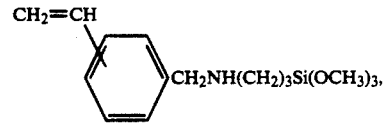
CH$_2$=CH—C$_6$H$_4$—CH$_2$NH(CH$_2$)$_3$Si(OCH$_3$)$_3$,

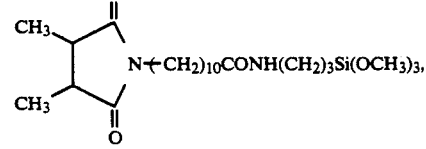
(CH$_3$)$_2$C(CO)$_2$N—(CH$_2$)$_{10}$CONH(CH$_2$)$_3$Si(OCH$_3$)$_3$, CH≡CSi(OC$_2$H$_5$)$_3$, CH$_2$=CHSi(OCOCH$_3$)$_3$, (C$_5$H$_7$O$_2$)$_2$Ti(OC$_3$H$_7$)$_2$, (C$_5$H$_7$O$_2$)$_2$V(OC$_3$H$_7$)$_2$, and (C$_5$H$_7$O$_2$)$_2$Ba(OC$_2$H$_5$)$_2$ 11. The process of claim 1 wherein said organic solvent is selected from the group consisting of methanol, ethanol, i-propanol, hexane, cyclohexane, benzene, toluene, 1,4-dioxane, tetrahydrofuran, methyl ethyl ketone, ethyleneglycol dimethyl ether, ethyleneglycol monomethyl ether, ethyleneglycol diethyl ether, propyleneglycol monomethyl ether, acetylacetone, N,N-dimethylformamide and monoethanol amine.

12. The process of claim 1 wherein the hydrolysis is conducted in the presence of water.

13. The process of claim 1 wherein said metal surface is a pure metal surface of aluminum, iron, copper, titanium, zirconium or the alloy thereof.

14. The process of claim 9 wherein said compound of M(OR)$_n$ is selected from the group consisting of $$Al(OCH(CH_3)_2)_3, Si(OCH_3)_4, Si(OC_2H_5)_4, Si(OCOCH_3)_4,$$

$$Si(OC_3H_7)_4, Si(OCH(CH_3)_2)_4, Si(OC_4H_9)_4,$$

$$Si(OCH_2CH(C_2H_5)_2)_4, Si(OCH_2CH(C_2H_5)(C_4H_9))_4,$$

Ti(OC$_3$H$_7$)$_4$, Ti(OC$_4$H$_9$)$_4$, Zr(OC$_3$H$_7$)$_4$, V(OC$_2$H$_5$)$_5$, and W(OC$_2$H$_5$)$_6$.

* * * * *